United States Patent
Rohrmann et al.

[11] Patent Number: 6,051,522
[45] Date of Patent: Apr. 18, 2000

[54] CATALYST WHICH CAN BE USED FOR THE PREPARATION OF OLEFINS DURING POLYMERIZATION

[75] Inventors: Jürgen Rohrmann, Kelkheim; Frank Küber, Oberursel, both of Germany

[73] Assignee: Targor GmbH, Germany

[21] Appl. No.: 08/464,459

[22] Filed: Jun. 5, 1995

Related U.S. Application Data

[63] Continuation of application No. 08/291,738, Aug. 17, 1994, abandoned, which is a continuation of application No. 07/980,993, Nov. 24, 1992, abandoned.

[30] Foreign Application Priority Data

Nov. 30, 1991 [DE] Germany .............................. 41 35 594

[51] Int. Cl.[7] .............................. B01J 31/00; B01J 37/00; C08F 4/02; C08F 4/60
[52] U.S. Cl. .................. 502/103; 502/117; 502/119; 502/121; 502/123; 502/124; 502/128; 502/152; 526/160; 526/943
[58] Field of Search .................................. 502/103, 117, 502/119, 121, 123, 128, 124, 152

[56] References Cited

U.S. PATENT DOCUMENTS

| | | | |
|---|---|---|---|
| 4,769,510 | 9/1988 | Kaminsky et al. | 526/160 |
| 4,892,851 | 1/1990 | Ewen et al. | 502/104 |
| 4,931,417 | 6/1990 | Miya et al. | 502/117 |
| 5,017,714 | 5/1991 | Welborn | 502/117 |
| 5,087,677 | 2/1992 | Brekner et al. | 526/160 |
| 5,103,030 | 4/1992 | Rohrmann et al. | 556/11 |
| 5,145,819 | 9/1992 | Winter et al. | 502/117 |
| 5,243,001 | 9/1993 | Winter et al. | 526/127 |
| 5,276,208 | 1/1994 | Winter et al. | 556/53 |
| 5,278,119 | 1/1994 | Turner et al. | 502/103 |
| 5,296,434 | 3/1994 | Karl et al. | 502/117 |
| 5,324,800 | 6/1994 | Welborn, Jr. | 526/160 |
| 5,329,033 | 7/1994 | Spaleck et al. | 556/53 |

(List continued on next page.)

FOREIGN PATENT DOCUMENTS

| | | |
|---|---|---|
| 0 129 368 | 12/1984 | European Pat. Off. . |
| 0 185 918 | 7/1985 | European Pat. Off. . |
| 0 284 708 | 10/1988 | European Pat. Off. . |

(List continued on next page.)

OTHER PUBLICATIONS

Bulletin de la Societe Chimique de France, "Etude de monomeres halogenes et de leur polymerisation cationique", No. 11, pp. 3092–3095, (1973) M. Olivier et al.

(List continued on next page.)

*Primary Examiner*—Mark L. Bell
*Assistant Examiner*—J. Pasterczyk
*Attorney, Agent, or Firm*—Connolly Bove Lodge & Hutz LLP

[57] ABSTRACT

A catalyst containing the combination which comprises:
(a) an aluminoxane, a compound of the formula $R_xNH_{4-x}$, $BR'_4$, $R_xPH_{4-x}$, $BR'_4$, $R_3CBR'_4$ or $BR'_3$, or a mixture thereof wherein X is an integer from 1 to 4 and the radicals R are identical or different and are a $C_1$–$C_{10}$-alkyl or a $C_6$–$C_{18}$-aryl or 2 radicals R together with the atom joining them form a ring, and the radicals R' are identical or different and are a $C_6$–$C_{18}$-aryl which optionally are substituted by alkyl, haloalkyl or fluorine, and
(b) a metallocene of the formula VI

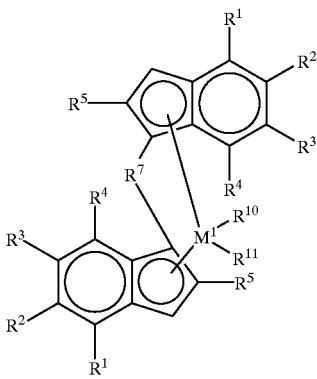

(VI)

in which
$M^1$ is titanium, zirconium, hafnium, vanadium, niobium or tantalum,
$R^1$ is $(C_3$–$C_{20})$alkyl, $(C_6$–$C_{14})$aryl, $(C_4$–$C_{10})$alkoxy, $(C_2$–$C_{10})$alkenyl, $(C_7$–$C_{20})$arylalkyl, $(C_7$–$C_{20})$alkylaryl, $(C_6$–$C_{10})$aryloxy, $(C_1$–$C_{10})$fluoroalkyl, $(C_6$–$C_{10})$halogenoaryl, $(C_2$–$C_{10})$alkynyl; a radical —$SiR^6_3$, in which $R^6$ is $(C_1$–$C_{10})$alkyl; a halogen atom; or an aromatic radical having 5 or 6 ring members in the ring, at lease one of which is a heteroatom,
$R^2$, $R^3$ and $R^4$ are identical or different and are hydrogen; $(C_1$–$C_{20})$alkyl, $(C_6$–$C_{14})$aryl, $(C_1$–$C_{10})$alkoxy, $(C_2$–$C_{10})$alkenyl, $(C_7$–$C_{20})$arylalkyl, $(C_7$–$C_{20})$alkylaryl, $(C_6$–$C_{10})$aryloxy, $(C_1$–$C_{10})$fluoroalkyl, $(C_6$–$C_{10})$halogenoaryl, $(C_2$–$C_{10})$alkynyl; a radical —$SiR^6_3$, in which $R^6$ is $(C_1$–$C_{10})$alkyl, a halogen atom, or a heteroaromatic radical which has 5 or 6 ring members and can contain one or more heteroatoms, or adjacent radicals $R^1$–$R^4$; with the atoms joining them, form one or more rings,
$R^5$ is hydrogen,
$R^7$ is a radical

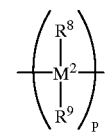

in which
$M^2$ is carbon, silicon, germanium or tin.

60 Claims, No Drawings

U.S. PATENT DOCUMENTS

| | | | |
|---|---|---|---|
| 5,455,365 | 10/1995 | Winter et al. | 502/117 |
| 5,455,366 | 10/1995 | Rohrmann et al. | 556/8 |
| 5,510,502 | 4/1996 | Sugano et al. | 502/103 |
| 5,514,760 | 5/1996 | Karl et al. | 526/127 |
| 5,561,093 | 10/1996 | Fujita et al. | 502/117 |
| 5,654,248 | 8/1997 | Kioka et al. | 502/103 |
| 5,672,668 | 9/1997 | Winter et al. | 526/127 |
| 5,693,836 | 12/1997 | Winter et al. | 556/11 |
| 5,700,749 | 12/1997 | Tsutsui et al. | 502/117 |
| 5,714,426 | 2/1998 | Tsutsui et al. | 502/117 |
| 5,723,640 | 3/1998 | Fukuoka et al. | 502/155 |

FOREIGN PATENT DOCUMENTS

| | | |
|---|---|---|
| 0 316 155 | 5/1989 | European Pat. Off. . |
| 0 320 762 | 6/1989 | European Pat. Off. . |
| 0 336 128 | 10/1989 | European Pat. Off. . |
| 0 344 887 | 12/1989 | European Pat. Off. . |
| 0 351 392 | 1/1990 | European Pat. Off. . |
| 0 366 290 | 5/1990 | European Pat. Off. . |
| 0 407 870 | 1/1991 | European Pat. Off. . |
| 0 426 637 | 5/1991 | European Pat. Off. . |
| 0 426 638 | 5/1991 | European Pat. Off. . |
| 0 426 643 | 5/1991 | European Pat. Off. . |
| 0 427 697 | 5/1991 | European Pat. Off. . |
| 0 433 990 | 6/1991 | European Pat. Off. . |
| 0 442 725 | 8/1991 | European Pat. Off. . |
| 0 485 821 | 5/1992 | European Pat. Off. . |
| 0 485 823 | 5/1992 | European Pat. Off. . |
| 0 500 005 | 8/1992 | European Pat. Off. . |
| 0 529 908 | 3/1993 | European Pat. Off. . |
| 37 26 067 | 2/1989 | Germany . |

OTHER PUBLICATIONS

J. Org. Chem., "Friedel–Crafts Reactions of Ethyl Cyclopropanecarboxylate", vol. 46, pp. 3758–3760 (1981), H. Pinniok et al.

Soga, K. et al., Macromolecules, "Perfect Conversion of Aspecific Sites into Isopecific Sites in Ziegler–Natta Catalysts", vol. 22, pp. 3824–3826 (1989).

J. Org. Chem., "Friedel–Crafts Chemistry. A Mechanistic Study of the Reaction of 3–Chloro–4'–fluoro–2–methylpropiophenone with $AlCl_3$ and $AlCl_3$–$CH_3NO_2$", vol. 43, No. 16, pp. 3126–3131 (1978) S. Pines et al.

Miyamota, T.K., et al., Chemistry Letters, The Chemical Society of Japan, "A Bulky Ligand and its Organometallic Compound: Synthesis of Heptamethylidene and a Ferrocene–Type Complex, $Fe(n^5–C_9Me_7)_2$", pp. 729–730 (1981).

Adcock et al., Austr. J. Chem., vol. 29, "Substituent Effects by $^{19}F$ Nuclear Magnetic Resonance: Polar and $\pi$–Electron Effects", pp. 2571–2581.

Marechal et al., Bull. Soc. Chim. Fr. 6, "Homopolymerisation cationlique des dimethyl–4,7,dimethyl–4,6 et dimethyl–5,6 indenes", No. 348, pp. 1981–1989, (1969).

Spaleck et al., New J. Chem., "Stereorigid Metallocenes: Correlations Between Structure and Behaviour in Homopolymerizations of Propylene", vol. 14, pp. 499–403 (1990).

Röll, V.W., et al., Angew. Chem., "Stereo– und Regioselektivitat von chiralen, alkylsubstituierten ansa–Zirconocen–Katalysatoren bei der Methylalumoxan–aktivierten Propen–Polymerization", vol. 102, No. 3, pp. 339–341 (1990).

Piccoliovazzi, N. et al., Organometallics, "Electronic Effects in Homogeneous Indenylzirconium Ziegler–Natta Catalysts", vol. 9, pp. 3098–3105 (1990).

Chemical Abstracts 90:567 103691p; (1978).

Criegee et al., Chem. Ber., vol. 94, "Uber den Nickelkomplex $C_{18}H_{22}Ni$ und den daraus gewonnenen Kohlenwasserstoff $C_{13}H_{18}$", pp. 3461–3468 (1964).

Hart et al., Notes, J. Am. Chem. Soc., vol. 72, "Acylation–Alkylation Studies", pp. 3286–3287 (1950).

Katz, Thomas J., J. Am. Chem. Soc., "Asymmetric Synthesis of Helical Metallocenes", vol. 108, 1986, pp. 179–181.

Ewen, J.A., et al, J. Am. Chem. Soc., Crystal Structures and Sterospecific Propylene Polymerizations with Chiral Hafnium Metallocene Catalysts, vol. 109, 1987, pp. 6544–6545.

CATALYST WHICH CAN BE USED FOR THE PREPARATION OF OLEFINS DURING POLYMERIZATION

This application is a continuation of application Ser. No. 08/291,738 filed Aug. 17, 1994, now abandoned which is a continuation of Ser. No. 07/980,993 filed Nov. 24, 1992 now abandoned.

The present invention relates to a simple process for the preparation of indene derivatives substituted on the five- and six-membered rings.

Compounds of this type are important intermediate products in the preparation of metallocene complexes. In particular, the corresponding bridged, chiral zirconium derivatives are of great importance as highly active catalysts in olefin polymerization (cf. EP-A 129 368). The properties of the catalysts can be influenced in a controlled manner by varying the ligand system, for example by substitution. It is thereby possible to modify the polymer yield, the molecular weight, the tacticity or the melting point of the polymers to the desired extent (New J. Chem. 14 (1990) 499; Organomet. 9 (1990) 3098; Angew. Chem. 102 (1990) 339; EP-A 316 155; and EP-A 351 392).

Indenes furthermore can also be employed as monomers in homopolymerization or copolymerization with other olefins (cf. Macromol. 22 (1989) 3824; and Bull. Soc. Chim. Fr. 6 (1969) 2039).

However, the few substituted indenes described in the literature as a rule are accessible only in low yields via multi-stage syntheses. They are usually obtained from the correspondingly substituted 1-indanones by reduction and subsequent dehydration. The corresponding indanones are obtainable in multi-stage syntheses starting from substituted aromatics (Bull. Soc. Chim. Fr. 6 (1969) 1981; Acta Chem. Scand. B 30 (1976) 527; Austr. J. Chem. 29 (1970) 2572; Chem. Lett. (1981) 729; and Ber. 97(12) (1964) 3461).

Certain substitution patterns moreover are not accessible by this route.

There was the task of discovering a process for the preparation of the abovementioned indenes which avoids the disadvantages known from the prior art. Such indenes allow access to novel metallocene complexes.

It has been found that aromatics of the following formula I react with derivatives of propionic acid carrying a leaving group in the α-position and with a Friedel-Crafts catalyst to give substituted 1-indanones in high yields. This result was completely unexpected, since these products would have been expected only with derivatives of propionic acid which carry a leaving group in the β-position (cf. J. Amer. Chem. Soc. 72 (1950) 3286).

Moreover, this synthesis is a one-stage process which is easy to handle industrially. The indanones can then be converted into the corresponding indenes by known methods. At the same time, the process according to the invention allows the preparation of novel compounds of the structure type mentioned.

The present invention therefore relates to a process for the preparation of a compound of the formula IV or an isomer thereof of formula IVa

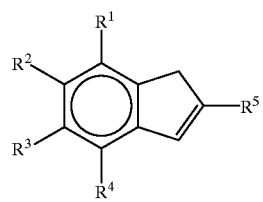

(IV)

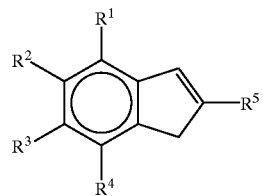

(IVa)

in which $R^1$, $R^2$, $R^3$, $R^4$ and $R^5$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$-fluoroalkyl, $(C_6-C_{10})$halogenoaryl, $(C_2-C_{10})$alkynyl, a radical $-SiR^6_3$, in which $R^5$ is $(C_1-C_{10})$alkyl, a halogen atom or a heteroaromatic radical which has 5 or 6 ring members and can contain one or more heteroatoms, or adjacent radicals $R^1-R^4$, with the atoms joining them, form one or more rings, which comprises reacting a compound of the formula I

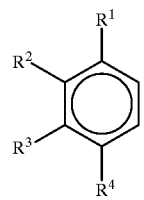

(I)

with a compound of the formula II

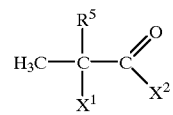

(II)

or an anhydride thereof, in the presence of a Friedel-Crafts catalyst to give a compound of the formula III or of the formula IIIa

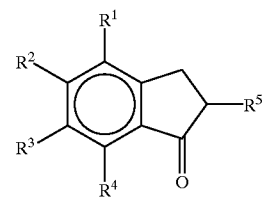

(III)

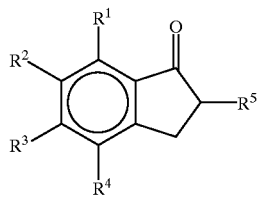

(IIIa)

in which $R^1$–$R^5$ have the meanings given and $X^1$ and $X^2$ are identical or different and are a nucleophilic leaving group, and converting this into the compound of the formula IV or IVa by reduction and dehydration by known methods.

In these formulae, alkyl is straight-chain or branched alkyl. Halogen is fluorine, chlorine, bromine or iodine, in particular fluorine or chlorine. Examples of hetero-aromatic radicals are thienyl, furyl or pyridyl.

The indanones can be obtained in the form of two structural isomers of the formula III and IIIa, depending on the substitution pattern on the aromatic radical. These isomers can be reduced, in the pure form or as a mixture, with reducing agents such as $NaBH_4$ or $LiAlH_4$ by methods which are known from the literature, to give the corresponding indanols, which can then be dehydrated with acids, such as sulfuric acid, oxalic acid or p-toluenesulfonic acid, or by treatment with dehydrating substances, such as magnesium sulfate, sodium sulfate, aluminum oxide, silica gel or molecular sieves, to give indenes of the formula IV or IVa (Bull. Soc. Chim. Fr. 11 (1973) 3092; Organomet. 9 (1990) 3098 and the embodiment examples).

$X^1$ and $X^2$ are preferably a halogen atom, a hydroxyl group, a tosyl group or a $(C_1$–$C_{10})$alkoxy group; in particular a halogen atom, particularly preferably bromine or chlorine.

Suitable Friedel-Crafts catalysts are, for example, $AlCl_3$, $AlBr_3$, $FeCl_3$, $SbCl_5$, $SnCl_4$, $BF_3$, $TiCl_4$, $ZnCl_2$, HF, $H_2SO_4$, polyphosphoric acid, $H_3PO_4$ or an $AlCl_3/NaCl$ melt; in particular $AlCl_3$.

In the formulae IV and IVa, preferably, $R^1$, $R^2$, $R^3$ and $R^4$ are identical or different and are hydrogen, $(C_1$–$C_{10})$alkyl, $(C_6$–$C_{14})$aryl, $(C_1$–$C_4)$alkoxy, $(C_2$–$C_6)$alkenyl, $(C_1$–$C_6)$fluoroalkyl, a halogen atom or a heteroaromatic radical which has 5 or 6 ring members and can contain one or more heteroatoms, or adjacent radicals $R^1$–$R^4$, with the atoms joining them, form a ring, and $R^5$ is $(C_1$–$C_{10})$alkyl.

In particular, $R^1$, $R^2$, $R^3$ and $R^4$ are identical or different and are hydrogen or $(C_1$–$C_{10})$alkyl, or the radicals $R^1$ and $R^2$ or $R^3$ and $R^4$, with the atoms joining them, form a ring, and $R^5$ is methyl.

The starting compounds of the formulae I and II are known and are commercially obtainable, or they can be prepared by processes which are known from the literature.

The reaction is carried out in an inert solvent. Methylene chloride or $CF_2$ is preferably employed. If the starting components are liquid, a solvent can also be dispensed with.

The molar ratios of the starting compounds, including the Friedel-Crafts catalyst, can vary within wide limits. The molar ratio of compound I:II:catalyst is preferably 1:0.5–1.5:1.5; in particular 1:1:2.5–3.

The reaction temperature is preferably 0° C. to 130° C., in particular 25° C. to 80° C.

The reaction times as a rule vary between 30 minutes and 100 hours, preferably between 2 hours and 30 hours.

Preferably, a mixture of compounds I and II is initially introduced into the reaction vessel and the Friedel-Crafts catalyst is metered in. The reverse sequence of addition is also possible.

The indanones of the formula III or IIIa can be purified by distillation, column chromatography or by crystallization.

The substituted indenes can be obtained as double bond isomers (IV/IVa). These can be purified from by-products by distillation, column chromatography or crystallization.

The process according to the invention is distinguished in partcular in that variously substituted indenes can be obtained in a high yield in a simple and short synthesis. The substitution pattern on the five- and six-membered ring can be varied within a very wide range in this process. This means that novel indene derivatives are also accessible.

The present invention furthermore relates to the use of the indene derivatives IV/IVa as an intermediate product in the preparation of metallocene complexes, in particular of those of the following formula VI.

The metallocenes of the formula VI are novel and the present invention likewise relates to them.

(VI)

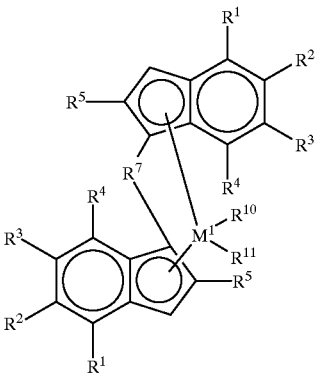

in which $M^1$ is titanium, zirconium, hafnium, vanadium, niobium or tantalum, $R^1$, $R^2$, $R^3$, $R^4$ and $R^5$ are identical or different and are hydrogen, $(C_1$–$C_{20})$alkyl, $(C_6$–$C_{14})$aryl, $(C_1$–$C_{10})$alkoxy, $(C_2$–$C_{10})$alkenyl, $(C_7$–$C_{20})$arylalkyl, $(C_7$–$C_{20})$alkylaryl, $(C_6$–$C_{10})$aryloxy, $(C_1$–$C_{10})$fluoroalkyl, $(C_6$–$C_{10})$halogenoaryl, $(C_2$–$C_{10})$alkynyl, a radical —$SiR^6_3$, in which $R^6$ is $(C_1$–$C_{10})$alkyl, a halogen atom or a heteroaromatic radical which has 5 or 6 ring members and can contain one or more heteroatoms, or adjacent radicals $R^1$–$R^4$, with the atoms joining them, form one or more rings, $R^7$ is a radical 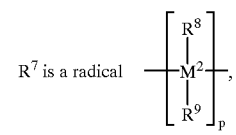, in which $M^2$ is carbon, silicon, germanium or tin, $R^8$ and $R^9$ are identical or different and are hydrogen, $(C_1$–$C_{20})$alkyl, $(C_6$–$C_{14})$aryl, $(C_1$–$C_{10})$alkoxy, $(C_2$–$C_{10})$alkenyl, $(C_7$–$C_{20})$arylalkyl, $(C_7$–$C_{20})$alkylaryl, $(C_6$–$C_{10})$aryloxy, $(C_1$–$C_{10})$fluoroalkyl, $(C_6$–$C_{10})$halogenoaryl, $(C_2$–$C_{10})$alkynyl or halogen, or $R^8$ and $R^9$, together with the atom joining them, form a ring, p is 0, 1, 2 or 3 and $R^{10}$ and $R^{11}$ are identical or different and are hydrogen, $(C_1$–$C_{10})$alkyl, $(C_1$–$C_{10})$alkoxy, $(C_6$–$C_{10})$aryl, ($C_6$–$C_{10}$)aryloxy, ($C_2$–$C_{10}$)alkenyl, ($C_7$–$C_{40}$)arylalkyl, ($C_7$–$C_{40}$)alkylaryl, ($C_8$–$C_{40}$)arylalkenyl, hydroxyl or a halogen atom.

Preferably, $M^1$ is zirconium or hafnium, in particular zirconium, $R^1$, $R^2$, $R^3$ and $R^4$ are identical or different and are hydrogen, ($C_1$–$C_{10}$)alkyl, ($C_6$–$C_{14}$)aryl, ($C_1$–$C_4$) alkoxy, ($C_2$–$C_6$)alkenyl, ($C_1$–$C_6$)fluoroalkyl, a halogen atom or a heteroaromatic radical which has 5 or 6 ring members and can contain one or more heteroatoms, and $R^5$ is ($C_1$–$C_{10}$)alkyl, or adjacent radicals $R^1$–$R^4$, with the atoms joining them, form a ring, $M^2$ is carbon or silicon, in particular silicon, $R^8$ and $R^9$ are identical or different and are hydrogen, ($C_1$–$C_6$)alkyl, ($C_6$–$C_{10}$)aryl, ($C_1$–$C_6$)alkoxy, ($C_2$–$C_4$)alkenyl, ($C_7$–$C_{10}$)arylalkyl or ($C_7$–$C_{10}$)alkylaryl, or $R^8$ and $R^9$, together with the atom joining them, form a ring, p is 1 or 2, preferably 1, and $R^{10}$ and $R^{11}$ are identical or different and are hydrogen, ($C_1$–$C_3$)alkyl, in particular methyl, ($C_1$–$C_3$)alkoxy, ($C_6$–$C_8$)aryl, ($C_6$–$C_8$)aryloxy, ($C_2$–$C_4$)alkenyl, ($C_7$–$C_{10}$)arylalkyl, ($C_7$–$C_{10}$)alkylaryl, ($C_8$–$C_{12}$)arylalkenyl or a halogen atom, preferably chlorine.

Preferably, the radicals $R^{10}$ and $R^{11}$ are identical and are chlorine or methyl. $M^2$ is, in particular, silicon, and the radicals $R^8$ and $R^9$ are identical or different and are preferably ($C_1$–$C_6$)alkyl, preferably methyl, or ($C_6$–$C_{10}$)aryl.

Furthermore, for the compounds of the formula VI, $R^5$ and $R^3$; $R^1$, $R^3$ and $R^5$; $R^1$, $R^2$, $R^3$ and $R^5$ or all the radicals $R^1$–$R^5$ are preferably other than hydrogen and are preferably ($C_1$–$C_4$)alkyl. Particularly preferably, the radicals $R^1$, $R^3$ and $R^5$ are other than hydrogen, are identical or different and are ($C_1$–$C_4$)alkyl.

The preferred substitution patterns on the indenyl radicals are therefore 2,6-, 2,4,6-, 2,4,5-, 2,4,5,6- and 2,4,5,6,7-, in particular 2,4,6- and 2,4,5-. The 2-position here on the indenyl radicals ($R^5$) is preferably substituted by a methyl group. Furthermore, for the compounds of the formula VI, the indenyl radicals are benzo-fused.

The compounds VI mentioned in the embodiment examples are of particular importance.

Starting from the indenes of the formulae IV and IVa, which can be employed as an isomer mixture, the preparation of the metallocenes VI proceeds by processes which are known from the literature (cf. AU-A-31478/89, J. Organomet. Chem. 342 (1988) 21, EP-A 284 707 and the embodiment examples) in accordance with the following equation:

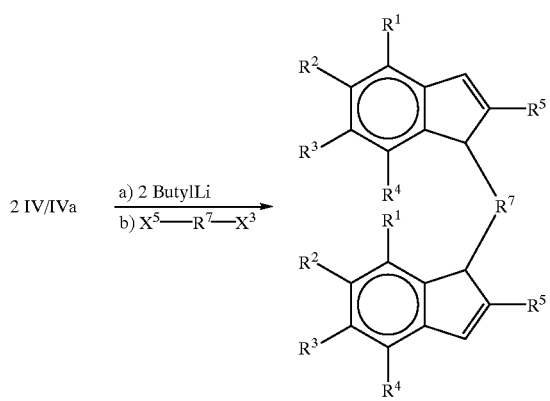

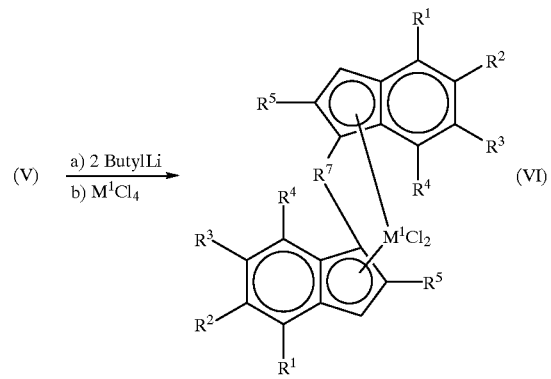

($X^3$=a nucleophilic leaving group, such as, for example, Cl, Br or O-tosyl).

The metallocene halides of the formula VI can be derivatized by methods which are known from the literature, for example by reactions with alkylating agents, such as lithiumalkyls, to give the corresponding mono- or dialkyl compounds (J. Amer. Chem. Soc. 95 (1973) 6263).

The bridged ligand systems of the formula V can be obtained as structural isomers, depending on the substitution pattern of the indene. If these isomers are not separated, structural isomers of metallocenes of the formula VI are formed. The metallocenes of the formula VI are obtained as a mixture of the racemic form with the meso form. The separation of the isomeric forms, in particular the removal of the meso form, which is undesirable for the olefin polymerization, is known in principle (AU-A-31478/89; J. Organomet. Chem. 342 (1988) 21; and EP-A 284 707). It is as a rule carried out by extraction or recrystallization using various solvents.

The present invention furthermore relates to the use of the compounds of the formula VI as catalyst components in olefin polymerization.

The metallocenes VI are highly active catalysts and are suitable, for example, for the preparation of olefin polymers of high isotacticity and high molecular weight.

The polymerization or copolymerization is carried out in a known manner in solution, in suspension or in the gas phase, continuously or discontinuously, in one or more stages, at a temperature of 0 to 150° C., preferably 30 to 80° C. Olefins of the formula $R^a$—CH=CH—$R^b$ are polymerized or copolymerized. In this formula, $R^a$ and $R^b$ are identical or different and are a hydrogen atom or an alkyl radical having 1 to 14 carbon atoms. However, $R^a$ and $R^b$, with the carbon atoms joining them, can also form a ring. Examples of such olefins are ethylene, propylene, 1-butene, 1-hexene, 4-methyl-1-pentene, 1-octene, norbornene, dimethaneoctahydronaphthalene or norbornadiene. In particular, propylene and ethylene are polymerized (cf., for example, EP-A 129 368).

Aluminoxanes are preferably used as cocatalysts (cf. EP-A 129 368; Polyhedron 9 (1990) 429 and the embodiment examples).

According to the invention, instead of or in addition to an aluminoxane, compounds of the formulae $R_xNH_{4-x}BR'_4$, $R_xPH_{4-x}BR'_4$, $R_3CBR'_4$ or $BR'_3$ can be used as suitable co-catalysts. In these formulae, x is a number from 1 to 4, preferably 3, the radicals R are identical or different, preferably identical, and are $C_1$–$C_{10}$-alkyl or $C_6$–$C_{18}$-aryl, or two radicals R, together with the atom joining them, form a ring, and the radicals R' are identical or different, preferably identical, and are $C_6$–$C_{18}$-aryl, which can be substituted by alkyl, haloalkyl or fluorine (EP-A 277 003, 277 004, 426 638 and 427 697).

The following examples serve to illustrate the invention in more detail.

EXAMPLE A 2,5,7-Trimethyl-1-indanone (1)

107 g (810 mmol) of $AlCl_3$ are slowly added to a solution of 34.4 g (324 mmol) of m-xylene (99% pure) and 74 g (324 mmol) of 2-bromoisobutyryl bromide (98% pure) in 600 ml of analytical grade methylene chloride via a solids metering funnel at room temperature, while stirring vigorously, whereupon vigorous evolution of gas started. The mixture was stirred at room temperature for 15 hours, poured onto ice-water, which was acidified with 25 ml of concentrated HCl, and extracted several times with ether. The combined organic phases were washed first with a saturated $NaHCO_3$ solution and then with a saturated NaCl solution and dried with magnesium sulfate. The oil which remained after the solvent had been stripped off under reduced pressure was distilled over a short distillation bridge. 52.4 g of the indanone 1 passed over at 81–90° C./0.1–0.2 mbar in the form of a colorless oil which crystallized at room temperature. The yield was 93%.

$^1$H-NMR spectrum (100 MHz, $CDCl_3$): 7.05 (1,s), 6.87 (1,s), 3.25 (1,q), 2.43–2.80 (2,m), 2.57 (3,s), 2.35 (3,s), 1.25 (3,d). Mass spectrum: 174 $M^+$, expected disintegration pattern.

EXAMPLE B 2,4,6-Trimethylindene (2)

20.4 g (117 mmol) of 2,5,7-trimethyl-1-indanone (1) were dissolved in 300 ml of a mixture of tetrahydrofuran/methanol (2:1), and 6.6 g (175 mmol) of $NaBH_4$ were added at room temperature. The mixture was stirred for a further hour, 50 ml of half-concentrated HCl were added and the mixture was extracted with ether. The combined organic phases were dried over sodium sulfate and freed from the solvent. The residue was transferred to a distillation apparatus, and 13 g of magnesium sulfate were added. A vacuum of about 10 mbar was applied and the mixture was heated up until the product distilled over (130–150° C.). Distillation gave 17.7 g of the indene 2 as a colorless oil. The yield was 96%.

$^1$H-NMR spectrum (100 MHz, $CDCl_3$): double bond isomers A:B=2:1; Isomer A: 6.97 (1,s), 6.80 (1,s), 6.50 (1,m), 3.20 (2,m), 2.1–2.3 (9,m). Isomer B: 6.87 (1,s), 6.70 (1,s), 6.37 (1,m), 3.07 (2,m), 2.1–2.3 (9,m). Mass spectrum: 158 $M^+$, expected disintegration pattern.

EXAMPLE C

2-Methyl-5,7-diisopropyl-1-indanone (3) and 2-methyl-4,6-diisopropyl-1-indanone (3a)

174 g (1300 mmol) of $AlCl_3$ were slowly added to a solution of 84.8 g (523 mmol) of 1,3-diisopropylbenzene and 120 g (523 mmol) of 2-bromoisobutyryl bromide (98% pure) in 600 ml of analytical grade methylene chloride via a solids metering funnel at room temperature. The mixture was heated under reflux for a further 20 hours and then worked up analogously to Example A. The crude product was chromatographed on 3 kg of silica gel 60. The indanones 3 and 3a were able to be eluted separately with a mobile phase mixture of hexane/15% ethyl acetate. Using the same mobile phase, the compound 2-methyl-5-isopropyl-1-indanone followed as a by-product in a further zone. However, separation of the two isomers is not necessary for the further reactions. The overall yield was 93 g (78%).

$^1$H-NMR spectrum (360 MHz, $CDCl_3$): isomer mixture (3:2) 7.49 (d), 7.36 (d), 7.13 (s), 7.10 (s), 4.15 (septet), 3.25–3.40 (m), 3.10 (septet), 2.90–3.00 (m), 2.60–2.73 (m), 1.22–1.30 (m).

Mass spectrum: 230 $M^+$, correct disintegration pattern.

EXAMPLE D

2-Methyl-4,6-diisopropylindene (4) and 2-methyl-5,7-diisopropylindene (4a), variant I 19.3 g (511 mmol) of $NaBH_4$ were added to a solution of 78.5 g (341 mmol) of the isomer mixture 3/3a in 700 ml of a solvent mixture of tetrahydrofuran/analytical grade methanol (2:1) at room temperature. After the mixture had been stirred at room temperature for 2 hours, 120–130 ml of half-concentrated HCl were added and the mixture was extracted with ether. The combined organic phases were dried with $Na_2SO_4$. The residue which remained after the solvent had been stripped off was taken up in 500 ml of methylene chloride, and the mixture was heated under reflux with 6.5 g (34 mmol) of p-toluenesulfonic acid for 15 minutes. The residue which remained after the solvent had been stripped off was chromatographed on 1.5 kg of silica gel 60. Using a mobile phase mixture of hexane/diisopropyl ether 20:1, 56 g of the isomer mixture 4/4a were able to be isolated in the form of a colorless oil. The overall yield was 86%.

$^1$H-NMR spectrum (100 MHz, $CDCl_3$): double bond isomers (1:1) 7.1 (m), 6.95 (m), 6.60 (m), 6.43 (m), 3.25 (br), 2.75–3.20 (m), 2.12 (d), 1.28 (d), 1.25 (d). Mass spectrum: 214 $M^+$, expected disintegration pattern.

EXAMPLE E

2-Methyl-4,6-diisopropylindene (4) and 2-methyl-5,7-diisopropylindene (4a), variant II 19.3 g (511 mmol) of $NaBH_4$ were added to a solution of 78.5 g (341 mmol) of the isomer mixture 3/3a in 700 ml of a solvent mixture of tetrahydrofuran/analytical grade methanol (2:1). After the mixture had been stirred at room temperature for 2 hours, 120–130 ml of half-concentrated HCl were added and the mixture was extracted with ether. The combined organic phases were dried with $Na_2SO_4$. The residue which remained after the solvent had been stripped off was transferred to a distillation apparatus, and 50 mg of magnesium sulfate were added. After a vacuum of about 1 mbar had been applied, the mixture was heated up until the product passed over (about 130° C.). 65 g of the isomer mixture 4/4a were obtained as a colorless oil. The yield was 90%.

EXAMPLE F

2-Methyl-1-indanone (5)

17.3 g (125 mmol) of $AlCl_3$ were added to a solution of 3.91 g (50 mmol) of benzene in 30 ml of analytical grade methylene chloride, while cooling with ice. 11.9 g (52 mmol) of 2-bromoisobutyryl bromide were then added, and stirring was continued at 0° C. for 1 hour and at room temperature for 2 hours. The mixture was heated under reflux for a further 15 hours and then worked up analogously to Example A. The crude product was chromatographed on 100 g of silica gel (hexane/methylene chloride 1:1). The yield was 5.1 g (70%).

$^1$H-NMR spectrum (100 MHz, $CDCl_3$): 7.5 (m), 3.33 (q), 2.73 (m), 1.30 (d). Mass spectrum: 146 $M^+$, expected disintegration pattern.

EXAMPLE G

2-Methylindene (6)

Analogously to Example D, 5.0 g (34 mmol) of 2-methyl-1-indanone (5) were reduced with 1.94 g (51 mmol) of $NaBH_4$. The alcohol, which was not purified further, was then further reacted in the presence of 0.2 g of p-toluenesulfonic acid in 100 ml of toluene at 80° C. Chromatography on 100 g of silica gel (hexane/methylene chloride 9:1) gave 3.68 g (82%) of 2-methylindene (6).

$^1$H-NMR spectrum (100 MHz, CDCl$_3$): 7.2 (4,m), 6.45 (1,m), 3.25 (2,m), 2.1 (3,m). Mass spectrum: 130 M$^+$, expected disintegration pattern.

EXAMPLE H
2-Methyl-5-isobutyl-1-indanone (7)

17.3 g (125 mmol) of AlCl$_3$ were added to a solution of 6.71 g (50 mmol) of isobutylbenzene in 30 ml of analytical grade methylene chloride, while cooling with ice. 11.9 g (52 mmol) of 2-bromoisobutyryl bromide were then added rapidly, and stirring was continued at 0° C. for 1 hour and at room temperature for 2 hours. The mixture was heated under reflux for a further 15 hours and then worked up analogously to Example A. The crude product was chromatographed on 100 g of silica gel (hexane/methylene chloride 1:1). The yield was 8.42 g (83%).

$^1$H-NMR spectrum (100 MHz, CDCl$_3$): 7.7 (m), 7.2 (m), 3.35 (q), 2.70 (m), 2.58 (d), 1.95 (q), 1.25 (d), 0.93 (d). Mass spectrum: 202 M$^+$, expected disintegration pattern.

EXAMPLE J
2-Methyl-6-isobutylindene (8)

Analogously to Example D, 8.3 g (41 mmol) of 2-methyl-5-isobutyl-1-indanone (7) were reduced with 2.4 g (62 mmol) of NaBH$_4$. The alcohol, which was not purified further, was then further reacted in the presence of 0.4 g of p-toluenesulfonic acid in 100 ml of toluene at 80° C. Chromatography on 400 g of silica gel (hexane) gave 7.17 g (95%) of 2-methyl-6-insobutylindene (8).

$^1$H-NMR spectrum (100 MHz, CDCl$_3$): 7.1 (m), 6.45 (m), 3.25 (m), 2.45 (d), 2.88 (q), 2.10 (d), 0.95 (d). Mass spectrum: 184 M$^+$, expected disintegration pattern.

EXAMPLE K
2,5,6,7-Tetramethyl-1-indanone (9)

17.3 g (125 mmol) of AlCl$_3$ were added to a solution of 6.01 g (50 mmol) of 1,2,3-trimethylbenzene in 30 ml of analytical grade methylene chloride, while cooling with ice. 11.9 g (52 mmol) of 2-bromoisobutyryl bromide were then added rapidly, and stirring was continued at 0° C. for 1 hour and at room temperature for 2 hours. The mixture was kept at room temperature for a further 15 hours and then worked up analogously to Example A. The crude product was purified by distillation (0.05 mm Hg/96–107° C.). The yield was 8.1 g (86%).

$^1$H-NMR spectrum (100 MHz, CDCl$_3$): 7.0 (m), 3.20 (q), 2.60 (m), 2.20 (m), 1.25 (d). Mass spectrum: 188 M$^+$, expected disintegration pattern.

EXAMPLE L
2,4,5,6-Tetramethylindene (10)

Analogously to Example D, 1.50 g (8 mmol) of 2,5,6,7-tetramethyl-1-indanone (9) were reduced with 0.45 g (12 mmol) of NaBH$_4$. The alcohol, which was not purified further, was then further reacted in the presence of 0.1 g of p-toluenesulfonic acid in 100 ml of toluene. Chromatography on 100 g of silica gel (hexane/methylene chloride 9:1) gave 0.88 g (65%) of 2,4,5,6-tetramethylindene (10).

$^1$H-NMR spectrum (100 MHz, CDCl$_3$): 7.0 (s), 6.45 (m), 3.25 (m), 2.60 (m), 2.20 (m), 2.10 (d). Mass spectrum: 170 M$^+$, expected disintegration pattern.

EXAMPLE M
Dimethylbis(2-methyl-4,6-diisopropylindenyl)silane (11)

9.2 ml (22.8 mmol) of a 2.5 M butyllithium solution in hexane were added to a solution of 4.9 g (22.8 mmol) of the isomer mixture 4/4a in 25 ml of tetrahydrofuran at 0° C. under Ar as an inert gas, and the mixture was heated under reflux for a further hour. The red solution was then added dropwise to a solution of 1.5 g (11.4 ml) of dimethyldichlorosilane in 10 ml of tetrahydrofuran, and the mixture was heated under reflux for 8 hours. The batch was poured onto ice-water and extracted with ether. The ether phase was dried over magnesium sulfate and evaporated under reduced pressure. The yellowish oil which remained was then chromatographed on 500 g of silica gel 60. With a mobile phase mlixture of hexane/5% methylene chloride, 1.4 g of the indene mixture 4/4a were able to be eluted first. The ligand system 11 followed with hexane/8% methylene chloride. The viscous oil which remained after the mobile phase had been stripped off was able to be crystallized by stirring with methanol in an ice bath. 3.1 g of a yellowish solid were obtained. The yield was 56%, or 84% with respect to the indene reacted.

$^1$H-NMR spectrum (100 MHz, CDCl$_3$): double bond isomers (3:1) 6.82–7.32 (m), 6.70 (m), 6.62 (m), 6.52 (m), 3.75 (s,br), 3.65 (s,br), 3.35 (s), 2.70–3.30 (m), 2.05–2.25 (m), 1.10–1.45 (m), 0.10–0.22 (m), –0.15 to –0.32 (m). Mass spectrum: 484 M$^+$, expected disintegration.

EXAMPLE N
Dimethylsilanediylbis(2-methyl-4,6-diisopropylindenyl)-zirconium dichloride (12)

6.3 ml (16.2 mmol) of a 2.5 M butyllithium solution in hexane were added to a solution of 3.1 g (6.5 mmol) of the ligand system 11 in 25 ml of diethyl ether at room temperature under Ar as the inert gas, and the mixture was stirred overnight. After addition of 10 ml of hexane, the beige-colored suspension was filtered and the residue was washed with 20 ml of hexane. The dilithium salt was dried under an oil-pump vacuum for a long time and then added to a suspension of 1.6 g (6.8 mmol) of ZrCl$_4$ in 30 ml of methylene chloride at –78° C. The mixture was warmed to room temperature in the course of 1 hour and stirred at this temperature for a further 30 minutes. After the solvent had been stripped off, the orange-brown residue was extracted with 50 ml of hexane. After the solvent had been stripped off, 2.6 g (60%) of the complex 12 were obtained in the form of a yellow powder. The ratio of the racemate to the meso form was 3:1. 1.3 g (30%) of the complex 12 were able to be obtained as the pure racemate by recrystallization from hexane (yellow crystalline powder).

$^1$H-NMR spectrum (100 MHz, CDCl$_3$): 7.27 (2, s,aromatic-H), 7.05 (2,s,aromatic-H), 6.80 (2,s,β-Ind-H), 2.6–3.2 (4,m,i-Pr-CH), 2.22 (6,s,Ind-CH$_3$), 1.15–1.40 (30,m, i-Pr-CH$_3$, Si-CH$_3$). Mass spectrum: 642 M$^+$ (with respect to $^{90}$Zr), expected isotope pattern, expected disintegration.

EXAMPLE O
Dimethylbis(2,4,6-trimethylindenyl)silane (13)

25.5 ml (63.7 mmol) of a 2.5 M butyllithium solution in hexane were added to a solution of 10.1 g (64 mmol) of the indene 2 in 50 ml of tetrahydrofuran at room temperature under Ar as the inert gas, and the mixture was heated under reflux for 1 hour. The solution thus obtained was added dropwise to a solution of 4.1 g (32 mmol) of dimethyldichlorosilane in 20 ml of tetrahydrofuran, and the mixture was heated under reflux for 3 hours. The reaction mixture was poured onto ice-water and extracted several times with ether. The combined organic phases were dried over sodium sulfate and evaporated under reduced pressure. The residue was chromatographed on 450 g of silica gel 60. With a mobile phase mixture of hexane/5% methylene chloride, 2.5 g of the indene 2 were able to be eluted first. 6.5 g of the ligand system 13 (isomers) followed with hexane/8% methylene chloride. The yield was 54%, or 72% with respect to the indene 2 reacted.

EXAMPLE P
Dimethylsilanediylbis(2,4,6-trimethylindenyl)zirconium dichloride (14)

6.6 ml (16.2 mmol) of a 2.5 M butyllithium solution in hexane were added to a solution of 2.0 g (5.4 mmol) of the ligand system 13 in 30 ml of diethyl ether at room temperature under Ar as the inert gas, and the mixture was stirred at this temperature for 5–6 hours. The solution was evaporated completely. The solid residue which remained was washed in portions with a total of 30 ml of hexane and dried under an oil-pump vacuum for a long time. The beige-colored powder thus obtained was added to a suspension of 1.23 g (5.5 mmol) of zirconium tetrachloride in 30 ml of methylene chloride at −78° C. After being warmed to room temperature, the reaction mixture was evaporated completely and the residue was dried under an oil-pump vacuum. The solid residue comprised a mixture of the racemic form with the meso form in a ratio of 1:1. This was first washed with a small amount of hexane. It was then extracted with a total of 120 ml of toluene. The solution was concentrated, and the residue was left to crystallize at −35° C. 800 mg (28%) of the zirconocene 14 were able to be obtained as the pure racemate in the form of orange-colored crystals.

$^1$H-NMR spectrum of the racemate (100 MHz, CDCl$_3$): 7.20 (s,2,aromatic-H), 6.97 (s,2,aromatic-H), 6.70 (s,2, β-Ind-H), 2.32 (s,6,CH$_3$), 2.27 (s,6,CH$_3$), 2.20 (s,6,CH$_3$), 1.27 (s,6,Si—CH$_3$). Mass spectrum: 530 M$^+$ (with respect to $^{90}$Zr), correct isotope pattern, expected disintegration.

EXAMPLE R
Methylphenylbis(2-methyl-4,6-diisopropylindenyl)silane (15)

18.6 ml (46 mmol) of a 2.5 M butyllithium solution in hexane were added to a solution of 10 g (46 mmol) of the indene 4/4a in 200 ml of tetrahydrofuran at room temperature under Ar as the inert gas, and the mixture was heated under reflux for 1 hour. The solution was added dropwise to a solution of 4.48 g (23 mmol) of methylphenyldichlorosilane in 30 ml of tetrahydrofuran at room temperature, and the mixture was heated under reflux for 3 hours. The mixture was poured onto ice-water and extracted several times with ether. The combined organic phases were dried with sodium sulfate and evaporated. The residue was chromatographed on 450 g of silica gel 60. With a mobile phase mixture of hexane/methylene chloride (10:1), 1.9 g of unreacted indene 4/4a were able to be recovered first. 7.4 g of the ligand system 15 (isomer mixture) then followed. The yield was 57%, or 73% with respect to the indene reacted.

EXAMPLE S
Methylphenylsilylbis(2-methyl-4,6-diisopropylindenyl)-zirconium dichloride (16)

11.2 ml (28 mmol) of a 2.5 M butyllithium solution in hexane were added to a solution of 7.4 g (13.5 mmol) of the ligand system 15 in 30 ml of diethyl ether at room temperature under Ar as the inert gas, and the mixture was stirred at room temperature for 16 hours. After the solvent had been stripped off, the residue which remained was dried at 40–50° C. for 3–4 hours, and then added to a suspension of 3.2 g (13.5 mmol) of zirconium tetrachloride in 40 ml of methylene chloride at −78° C. After the mixture had been warmed to room temperature, the solvent was stripped off under reduced pressure. The solid residue which remained was dried under an oil-pump vacuum and extracted with 100 ml of hexane. After the solvent had been stripped off, 5.4 g (55%) of the zirconocene 16 were obtained as a mixture of the racemic form with the meso form in a ratio of 2:1 (orange-brown crystalline powder). The pure racemic form is obtainable by recrystallization from hexane.

$^1$H-NMR spectrum of the isomer mixture (100 MHz, CDCl$_3$): 6.6–8.2 (m,aromatic-H,β-Ind-H), 2.5–3.2 (m,i-Pr-H), 2.52 (s,CH$_3$), 2.32 (s,CH$_3$), 2.20 (s,CH$_3$), 1.90 (s,CH$_3$), 1.0–1.5 (m,i-Pr-CH$_3$,Si-CH$_3$). Mass spectrum: 704 M$^+$ (with respect to $^{90}$Zr), correct isotope pattern, expected disintegration.

EXAMPLE T
1,2-Bis(2-methyl-4,6-diisopropylindenyl)ethane (17)

18.6 ml (46 mmol) of a 2.5 M butyllithium solution in hexane were added to a solution of 5.0 g (23.3 mmol) of the indene 4/4a in 50 ml of tetrahydrofuran at room temperature under Ar as the inert gas, and the mixture was heated under reflux for 1 hour. The solution was added to a solution of 2.18 g (11.0 mmol) of 1,2-dibromoethane at −78° C. The solution was warmed slowly to room temperature and stirred at this temperature overnight. The mixture was poured onto ice-water and extracted several times with ether. The combined organic phases were dried with sodium sulfate and evaporated. The residue was chromatographed on 450 g of silica gel 60. With a mobile phase mixture of hexane/methylene chloride (20:1 to 10:1), 1.2 g of unreacted indene 4/4a were able to be recovered first. 1.7 g of the ligand system 17 (colorless solid) then followed. The yield was 35%, or 45% with respect to the indene reacted.

EXAMPLE U
1,2-Ethanediylbis(2-methyl-4,6-diisopropylindenyl)-zirconium dichloride (18)

3.5 ml (8.8 mmol) of a 2.5 M butyllithium solution in hexane were added to a solution of 1.6 g (3.52 mmol) of the ligand system 17 in 20 ml of diethyl ether at room temperature under Ar as the inert gas, and the mixture was stirred overnight. The residue which remained after the solvent had been stripped off was washed with hexane and dried under an oil-pump vacuum for a long time. The powder thus obtained was added to a suspension of 815 mg (3.5 mmol) of zirconium tetrachloride in 15 ml of methylene chloride at −78° C. After the mixture had been warmed to room temperature, it was stirred for a further hour, and the solvent was removed under reduced pressure. The residue was dried under an oil-pump vacuum and extracted with toluene. Stripping off the solvent and washing with hexane gave 1.5 g (70%) of the zirconocene 18 as a mixture of the racemic with the meso form in a ratio of 2:1 (orange-colored powder). 700 mg (32%) of the pure racemate were able to be obtained by recrystallization from a toluene/hexane mixture.

$^1$H-NMR spectrum of the racemate (100 MHz, CDCl$_3$): 7.3 (s,aromatic-H), 7.0 (s,aromatic-H), 6.55 (s,β-Ind-H), 3.6 (s,C$_2$H$_4$), 2.6–3.2 (m,i-Pr-H), 2.2 (s,CH$_3$). Mass spectrum: 612 M$^+$ (with respect to $^{90}$Zr), correct isotope pattern, expected disintegration.

EXAMPLE V
2-Methyl-6,7-benzoindan-1-one (19a) and 2-methyl-4,5-benzoindan-1-one (19b)

27.5 g (207 mmol) of AlCl$_3$ were added to a solution of 10 g (83 mmol) of naphthalene and 19 g (83 mmol) of 2-bromoisobutyryl bromide in 200 ml of $CH_2Cl_2$ via a solids metering funnel at room temperature in the course of 30 minutes. After 4 hours, the mixture was worked up analogously to Example A. The crude product was filtered with ethyl acetate over a short column filled with silica gel. After the solvent had been stripped off, 15.5 g (95%) of the isomer mixture 19a/19b were obtained as a yellowish oil. The isomer ratio of 19a:19b was 1:2.

$^1$H-NMR spectrum (100 MHz, $CDCl_3$): 19a: 9.15 (m,1H), 7.40–8.10 (m,5H), 3.47 (dd,1H), 2.62–2.95 (m,2H), 1.37 (d,3H); 19b: 7.4–8.0 (m,6H), 3.7 (dd,1H), 2.75–3.10 (m,2H), 1.40 (d,3H). Mass spectrum: 196 M$^+$, expected disintegration pattern.

EXAMPLE W
2-Methyl-6,7-benzoindan-1-one (19a)

The same batch size as in Example V was chosen. The naphthalene was initially introduced into the reaction vessel together with the $AlCl_3$ in $CH_2Cl_2$, and bromoisobutyryl bromide was slowly added dropwise at room temperature. After 1.5 hours, the mixture was worked up as in Example V. Chromatography on silica gel 60 with a hexane/ethyl acetate mixture gave 11 g (67%) of the indanone 19a.

EXAMPLE X
2-Methyl-4,5-benzoindene (20a) and 2-methyl-6,7-benzoindene (20b)

2.2 g (59.5 mmol) of sodium borohydride were added in portions to a solution of 7.8 g (39.7 mmol) of the isomer mixture of the indanones 19a/19b (Example V) in 400 ml of a tetrahydrofuran/methanol mixture (2:1)at room temperature, and the mixture was stirred for 14 hours. The solution was poured onto ice-water acidified with HCl, and extracted with ether. The combined organic phases were washed several times with water and dried with sodium sulfate. The orange-colored oil which remained after the solvent had been stripped off was dissolved in 240 ml of toluene, and the solution was heated at 80° C. with 570 mg (3.15 mmol) of p-toluenesulfonic acid for 15 minutes. The solution was washed several times with water at room temperature, dried with sodium sulfate and evaporated. The residue was chromatographed on 300 g of silica gel 60. With a mobile phase mixture of hexane/diisopropyl ether (20:1), 4.7 g (65%) of the isomer mixture of the indenes 20a/20b in a ratio of 1:2 were able to be eluted (colorless oil).

$^1$H-NMR spectrum (360 MHz, $CDCl_3$): isomer mixture 7.2–8.1 (m), 7.05 (m), 6.57 (m), 3.57 (s), 3.42 (m), 2.25 (d), 2.20 (d). Molecular weight: 180 M$^+$, expected disintegration pattern.

EXAMPLE Y
Dimethylbis(2-methyl-4,5-benzoindenyl)silane (21)

10.2 ml (25.5 mmol) of a 2.5 M butyllithium solution in hexane were added to a solution of 4.6 g (25.5 mmol) of the isomer mixture of the indenes 20a/20b (Example X) in 50 ml of tetrahydrofuran at room temperature, and the mixture was heated under reflux for 1 hour. The red solution was then added dropwise to a solution of 1.55 g (12 mmol) of dimethyldichlorosilane in 10 ml of tetrahydrofuran at room temperature, and the mixture was heated under reflux for 5–6 hours. The reaction solution was poured onto ice-water and extracted several times with ether. The combined organic phases were dried with sodium sulfate and evaporated, and the residue was dried under an oil-pump vacuum. The residue was chromatographed on 300 g of silica gel 60. With a mobile phase mixture of hexane/3% ethyl acetate, 500 g of unreacted starting material 20a/20b were able to be eluted first. The ligand system 21 then followed with the same mobile phase. After the solvent had been stripped off, this ligand system was able to be crystallized by stirring with hexane. The yield was 1.7 g (34% with respect to Si, or 44% with respect to the 20a/20b reacted).

$^1$H-NMR spectrum (100 MHz, $CDCl_3$): diastereomers (1:1) 7.2–8.2 (m), 4.05 (s), 2.45 (d), 2.35 (d), –0.22 (s), –0.32 (s), –0.35 (s). Mass spectrum: 416 M$^+$, expected disintegration pattern and isotope pattern.

EXAMPLE Z
rac-Dimethylsilanediylbis(2-methyl-4,5-benzoindenyl)-zirconium dichloride (22)

4.0 ml (10.2 mmol) of a 2.5 M butyllithium solution in hexane were added to a solution of 1.7 g (4.1 mmol) of the ligand system 21 in 20 ml of tetrahydrofuran at room temperature under Ar as the inert gas, and the mixture was stirred at room temperature for 14 hours. The residue which remained after the solvent had been stripped off was dried under an oil-pump vacuum and washed with hexane. The pale brown powder thus obtained was dried under an oil-pump vacuum at 40–50° C. for several hours, and added to a suspension of 1.0 g (4.0 mmol) of zirconium tetrachloride in 25 ml of methylene chloride at –78° C. After the mixture had been warmed to room temperature, the solvent was stripped off and the residue was extracted with 20 ml of toluene in order to remove the meso form of the zirconocene 22. The residue of the toluene extract was then extracted with 40 ml of methylene chloride. The solution was concentrated to a small volume and left to crystallize at –35° C. A total of 970 mg (42%) of the zirconocene 22 were able to be isolated as the pure racemate in several fractions.

$^1$H-NMR spectrum of the racemate (300 MHz, $CDCl_3$): 7.96 (2,m), 7.78 (2,m), 7.60 (2,d), 7.48–7.56 (4,m), 7.36 (2,d), 7.27 (2,s,β-Ind-H), 2.37 (6,s,Ind-$CH_3$), 1.36 (6,s,Si-$CH_3$). Mass spectrum: 574 M$^+$, expected disintegration, expected isotope pattern.

EXAMPLE AA
2-Methyl-α-acenaphthindan-1-one (23)

29.7 g (129 mmol) of 2-bromoisobutyryl bromide were added to a solution of 20 g (129 mmol) of α-acenaphthene in 320 ml of methylene chloride at room temperature. 43.5 g (324 mmol) of $AlCl_3$ were then added via a solids metering funnel in the course of 15 minutes. After the mixture had been stirred for 30 minutes, it was poured into ice-water and extracted with methylene chloride. The organic phase was washed with water and an $NaHCO_3$ solution, and dried with $Na_2SO_4$. The residue which remained after the solvent had been stripped off was filtered over a short column with silica gel. 25 g (87%) of the indanone 23 were obtained with hexane/ethyl acetate (9:2).

$^1$H-NMR ($CDCl_3$, 100 MHz): 8.57 (d,1), 7.60 (t,1), 7.35 (d,1), 7.25 (s,1), 3.45 (q,1), 3.40 (s,4), 2.60–2.95 (m,2), 1.35 (d,3).

EXAMPLE BB
2-Methyl-α-acenaphthindene (24)

A solution of 20 g (90 mmol) of the compound 23 in 250 ml of a tetrahydrofuran/methanol mixture (2:1) was added dropwise to a suspension of 3.8 g (100 mmol) of $NaBH_4$ in 80 ml of tetrahydrofuran. The mixture was stirred at room temperature for 2 hours, and 100 ml of ethyl acetate and 100 ml of half-concentrated HCl were added. The mixture was heated under reflux for 10 minutes and extracted with ethyl acetate. The organic phase was washed with water and dried with $Na_2SO_4$. On concentration and cooling to –35° C., a total of 16.3 g (88%) of the compound 24 crystallized in several fractions.

$^1$H-NMR (CDCl$_3$, 100 MHz): 7.1–7.8 (m,4,aromatic-H), 6.97 (m,1,olefin-H), 3.37 (s,6,CH$_2$), 2.25 (d,3,CH$_3$).

EXAMPLE CC

Dimethylbis(2-methyl-α-acenaphthindenyl)silane (25)

10.8 g (52.4 mmol) of the compound 24 were deprotonated analogously to Example O and reacted with dimethyldichlorosilane. The organic phase was evaporated and the residue was chromatographed on silica gel. 6.2 g (51%) of the ligand system 25 were able to be obtained with hexane/4% ethyl acetate.

$^1$H-NMR (CDCl$_3$, 100 MHz): diastereomer pair 7.1–7.8 (m,aromatic-H), 4.0 (s,CH), 3.45 (s,CH$_2$), 2.47 (d,CH$_3$), 2.40 (d,CH$_3$), −0.25 (s,SiCH$_3$), −0.35 (s,SiCH$_3$), −0.37 (s,SiCH$_3$).

EXAMPLE DD rac-Dimethylsilanediylbis(2-methyl-α-acenaphthindenyl)-zirconium dichloride (26)

4.9 g (10.5 mmol) of the ligand system 25 were reacted analogously to Example P. The crude product, comprising the racemic form with the meso form in a ratio of 1:1, was recrystallized from chloroform. 1.3 g (20%) of the racemate 26 were obtained in the form of an orange-yellow powder.

$^1$H-NMR (CDCl$_3$, 100 MHz): 7.0–7.8 (m,aromatic-H), 3.1–3.4 (m,CH$_2$), 2.35 (s,CH$_3$), 1.35 (s,SiCH$_3$).

POLYMERIZATION EXAMPLES

EXAMPLE 1

A dry 24 dm$^3$ reactor was flushed with propylene and filled with 12 dm$^3$ of liquid propylene. 35 cm$^3$ of a toluene solution of methylaluminoxane (corresponding to 52 mmol of Al, average degree of oligomerization p=20) were then added and the batch was stirred at 30° C. for 15 minutes.

In parallel, 3.5 mg (0.005 mmol) of rac-dimethylsilyl(2-methyl-4,6-diisopropyl-1-indenyl)$_2$zirconium dichloride were dissolved in 13.5 cm$^3$ of a toluene solution of methylaluminoxane (20 mmol of Al) and preactivated by being left to stand for 15 minutes.

The wine-red solution was then introduced into the reactor, the mixture was heated to 75° C. (10° C./minute) by supplying heat, and the polymerization system was kept at 70° C., by cooling, for 1 hour. The polymerization was stopped by gassing off the excess monomer. 2.11 kg of polypropylene were obtained.

The activity of the metallocene was thus 603 kg of polypropylene/g of metallocene×hour.

Viscosity number=259 cm$^3$/g, M$_w$=305,000 g/mol; M$_w$/M$_n$=2.0; isotactic index=96.0%; bulk density=400 g/dm$^3$; melt flow index (230/5)=8.5 dg/minute.

COMPARISON EXAMPLE 1

Example 1 was repeated with the metallocene rac-dimethylsilyl(2-methyl-1-indenyl)$_2$zirconium dichloride. The metallocene activity was 395 kg of polypropylene/g of metallocene×hour.

Viscosity number=159 cm$^3$/g, M$_w$=158,000 g/mol; M$_w$/M$_n$=2.1 and the melt flow index (230/5) was 48 dg/minute. The isotactic index (II) was 96.0%.

COMPARISON EXAMPLE 2

Example 1 was repeated with the metallocene rac-dimethylsilyl(2-methyl-4-isopropyl-1-indenyl)$_2$zirconium dichloride.

The metallocene activity was 460 kg of polypropylene/g of metallocene×hour, viscosity number=152 cm$^3$/g, M$_w$=147,500 g/mol, M$_w$/M$_n$=2.3 and melt flow index (230/5)=51 dg/minute.

COMPARISON EXAMPLE 3

Example 1 was repeated with rac-dimethylsilyl(1-indenyl)$_2$zirconium dichloride. The metallocene activity was 695 kg of polypropylene/g of metallocene×hour.

Viscosity number=31 cm$^3$/g, M$_w$=18,500 g/mol, M$_w$/M$_n$=2.2, melt flow index (230/5) was no longer measurable.

COMPARISON EXAMPLE 4

Example 1 was repeated with the metallocene rac-dimethylsilyl(4,7-dimethyl-1-indenyl)$_2$zirconium dichloride. The metallocene activity was 195 kg of polypropylene/g of metallocene×hour, viscosity number=16 cm$^3$/g, M$_w$=9,500 g/mol, M$_w$/M$_n$=2.0, II=87%, the melt flow index (230/5) was not measurable.

The four comparison experiments show that polypropylenes prepared with the metallocenes substituted in various ways on the indenyl ligand and prepared with the unsubstituted metallocene show significant differences in molecular weight. Including the metallocene according to the invention from Example 1, the range extends from the wax range (Comparison Example 4) to the very high molecular weight polymer according to the invention (Example 1).

These experiments demonstrate the superiority of the metallocenes substituted in the 2,4,6-position.

What is claimed is:

1. A catalyst comprising the combination of components comprising at least one cocatalyst (a) combined with at least one metallocene compound (b) wherein the cocatalyst (a) comprises an aluminoxane, a compound of the formula R$_x$NH$_{4-x}$BR'$_4$, R$_x$, R$_3$CBR'$_4$ or BR'$_3$, wherein X is an integar from 1 to 4 and the radicals R are identical are different and or a C$_1$–C$_{10}$-alkyl or a C$_6$–C$_{18}$-aryl or 2 radicals R together with the atom joining them form a ring, and the radicals R' are identical or different and are a C$_6$–C$_{18}$-aryl which can be substituted by alkyl, haloalkyl or fluorine; and the metallocene compound (b) is of the formula VI selected from the following group consisting of the following 5 alternatives (i–v)

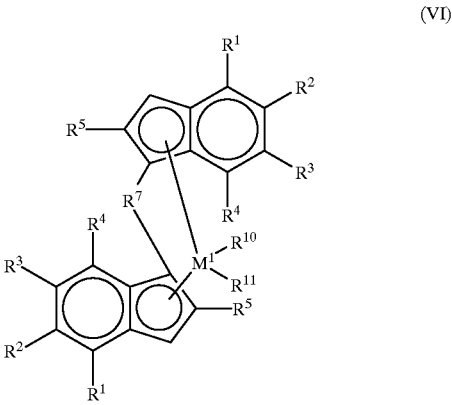

(VI)

in which

M$^1$ is titanium, zirconium, hafnium, vanadium, niobium or tantalum, $R^7$ is a radical

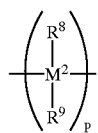

in which $M^2$ is carbon, silicon, germanium or tin;

$R^8$ and $R^9$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or $R^8$ and $R^9$, together with the atom joining them form a ring, and $R^{10}$ and $R^{11}$ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$arylalkenyl, hydroxyl or a halogen atom, with alternative (i) being, $R^1$, $R^2$, $R^3$, and $R^4$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6_3$, a halogen atom, or an aromatic radical having 5 or 6 ring members in the ring, at least one of which is a heteroatom, or adjacent radicals $R^1-R^4$ with the atoms joining them form one or more rings;

$R^5$ is $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6_3$, a halogen atom, or an aromatic radical having 5 or 6 ring members in the ring, at least one of which is a heteroatom and $R^6$ is $(C_1-C_{10})$alkyl, p is 0, with alternative (ii) being, $R^1$ is $(C_3-C_{20})$alkyl, $(C_6-C_{14})$aryl, $(C_4-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6_3$, a halogen atom, or an aromatic radical having 5 or 6 ring members in the ring, at least one of which is a heteroatom $R^2$, $R^3$ and $R^4$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6_3$, a halogen atom, or an aromatic radical having 5 or 6 ring members in the ring, at least one of which is a heteroatom: or adjacent radicals $R^1-R^4$ with the atoms joining them form one or more rings, $R^5$ is hydrogen, $R^6$ is $(C_1-C_{10})$alkyl; and p is 1, 2 or 3, with alternative (iii) being, $R^1$, $R^3$ and $R^4$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6_3$, a halogen atom, or an aromatic radical having 5 or 6 ring members in the ring, at least one of which is a heteroatom, or adjacent radicals $R^1-R^4$ with the atoms joining them form one or more rings;

$R^2$ is $(C_3-C_{20})$alkyl, $(C_6-C_{14})$aryl, $(C_4-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6_3$, a halogen atom, or an aromatic radical having 5 or 6 ring members in the ring, at least one of which is a heteroatom, and $R^5$ is hydrogen, $R^6$ is $(C_1-C_{10})$alkyl, and p is 1, 2 or 3, with alternative (iv) being, $R^1$, $R^2$ and $R^4$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6_3$, a halogen atom, or an aromatic radical having 5 or 6 ring members in the ring, at least one of which is a heteroatom, or adjacent radicals $R^1-R^4$ with the atoms joining them form one or more rings, $R^3$ is $(C_3-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6_3$, a halogen atom, or an aromatic radical having 5 or 6 ring members in the ring, at least one of which is a heteroatom;

$R^5$ is hydrogen, and $R^6$ is $(C_1-C_{10})$alkyl;

p is 1, 2 or 3; and with alternative (v) being, $R^1$, $R^2$ and $R^3$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6_3$, a halogen atom or an aromatic radical having 5 or 6 ring members in the ring, at least one of which is a heteroatom, or adjacent radicals $R^1-R^4$ with the atoms joining them form one or more rings;

$R^4$ is $(C_3-C_{20})$alkyl, $(C_6-C_{14})$aryl, $(C_4-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6_3$, a halogen atom, or an aromatic radical having 5 or 6 ring members in the ring, at least one of which is a heteroatom, and $R^5$ is hydrogen, $R^6$ is $(C_1-C_{10})$alkyl; and p is 1, 2 or 3.

2. A catalyst comprising the combination which comprises:

(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine, and (b) a metallocene of the formula VI

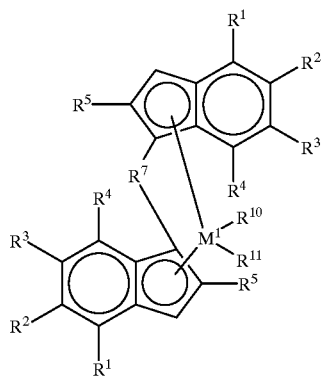

(VI)

in which
M¹ is titanium, zirconium, hafnium, vanadium, niobium or tantalum,
R¹, R² and R³ are identical or different and are hydrogen; $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$arylo $(C_1-C_{10})$fluoroalkyl, $(C_6-C_{10})$halogenoaryl, $(C_2-C_{10})$alkynyl; a radical —$SiR^6_3$, a halogen atom or an aromatic radical having 5 or 6 ring members in the ring, at least one of which is a heteroatom or adjacent radicals $R^1$–$R^4$ with the atoms joining them form one or more rings;
R⁴ is $(C_3-C_{20})$alkyl, $(C_6-C_{14})$aryl, $(C_4-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl; a radical —$SiR^6_3$, a halogen atom, or an aromatic radical having 5 or 6 ring members in the ring, at least one of which is a heteroatom,
R⁵ is hydrogen,
R⁶ is $(C_1-C_{10})$alkyl,
R⁷ is a radical

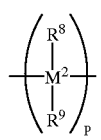

in which
M² is carbon, silicon, germanium or tin,
R⁸ and R⁹ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or
R⁸ and R⁹, together with the atom joining them form a ring,
p is 1, 2 or 3, and
R¹⁰ and R¹¹ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$ arylalkenyl or hydroxyl.

3. The catalyst as claimed in claim 2, wherein
M¹ is zirconium,
R¹, R² and R³ are identical or different and are hydrogen, $(C_1-C_{10})$alkyl, $(C_6-C_{14})$aryl, $(C_1-C_4)$alkoxy, $(C_2-C_6)$ alkenyl, $(C_1-C_6)$fluoroalkyl, a halogen atom, or an aromatic radical having 5 or 6 ring members in the ring, at least one of which is a heteroatom or adjacent radicals $R^1$–$R^4$; with the atoms joining them form a ring,
R⁴ is $(C_3-C_{10})$alkyl, $(C_6-C_{14})$aryl, $C_4$-alkoxy, $(C_2-C_6)$ alkenyl, $(C_1-C_6)$fluoroalkyl, a halogen atom, or an aromatic radical having 5 or 6 ring members in the ring, at least one of which is a heteroatom, and M² is silicon.

4. A catalyst comprising the combination which comprises:

(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine, and (b) a metallocene of the formula VI

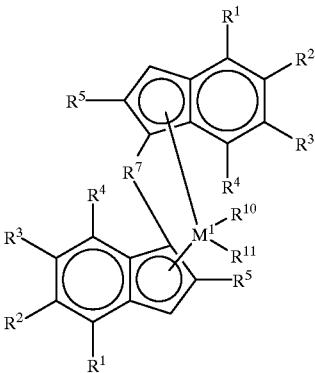

(VI)

in which
M¹ is titanium, zirconium, hafnium, vanadium, niobium or tantalum,
R¹, R² and R³ are identical or different and are hydrogen, $(C_1-C_{20})$alkyl, $(C_6-C_{14})$aryl, $(C_1-C_{10})$ alkoxy, $(C_2-C_{10})$alkenyl, $(C_7-C_{20})$alkylaryl, $(C_7-C_{20})$alkylaryl, $(C_6-C_{10})$aryloxy, $(C_1-C_{10})$ fluoroalkyl, $(C_6-C_{10})$halogenoaryl, $C_2-C_{10})$alkynyl; a radical —$SiR^6_3$, a halogen atom, or an aromatic radicals having 5 or 6 members in the ring, at least one of which is a heteroatom, or adjacent radicals $R^1$–$R^4$ with the atoms joining them form one or more rings;
R⁴ is $(C_1-C_{20})$alkyl; $(C_6-C_{14})$aryl; $(C_1-C_{10})$alkoxy; $(C_2-C_{10})$alkenyl; $(C_7-C_{20})$arylalkyl; $C_7-C_{20})$ alkylaryl; $(C_6-C_{10})$aryloxy; $(C_1-C_{10})$fluoroalkyl; $(C_6-C_{10})$halogenoaryl; $(C_2-C_{10})$alkynyl; a radical —$SiR^6_3$, a halogen atom, or an aromatic radical having 5 or 6 ring members in the ring, at least one of which is a heteroatom and
R⁵ is hydrogen,
R is $(C_1-C_{10})$alkyl, $R^7$ is a radical

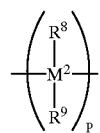

in which $M^2$ is carbon, silicon, germanium or tin, $R^8$ is a $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen, $R^9$ is hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or $R^8$ and $R^9$, together with the atom joining them form a ring, p is 1, 2 or 3, and $R^{10}$ and $R^{11}$ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$arylalkenyl, hydroxyl or a halogen atom.

5. The catalyst as claimed in claim 4, wherein $M^1$ is zirconium, $R^{10}$ and $R^{11}$ are chlorine, $R^1$, $R^2$ and $R^3$ are identical or different and are hydrogen, $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen atom, or an aromatic radical having 5 or 6 ring members in the ring, at least one of which is a heteroatom, $R^4$ is $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen atom, or an aromatic radical having 5 or 6 ring members in the ring, at least one of which is a heteroatom and $M^2$ is silicon.

6. The catalyst as claimed in claim 5, wherein $R^9$ is a $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen.

7. A catalyst comprising the combination which comprises:

(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine, and (b) a metallocene of the formula VI

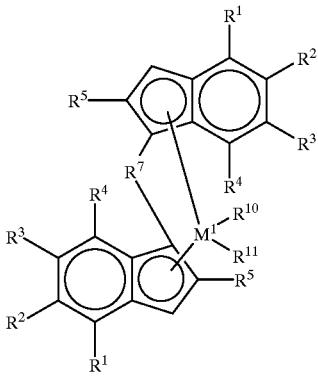

(VI)

in which $M^1$ is titanium, zirconium, hafnium, vanadium, niobium or tantalum, $R^1$, $R^2$ and $R^3$ are identical or different and are hydrogen, $(C_1-C_{20})$alkyl, $(C_6-C_{14})$aryl, $(C_1-C_{10})$arylalkyl, $(C_2-C_{10})$arylalkyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl; a radical —$SiR^6_3$, a halogen atom, or an aromatic radical having 5 or 6 ring members in the ring, at least one of which is a heteroatom or adjacent radicals $R^1-R^4$ with the atoms joining them form one or more rings;

$R^4$ is $(C_1-C_{20})$alkyl, $(C_6-C_{14})$aryl, $(C_1-C_{10})$alkoxy, $(C_2-C_{10})$alkenyl, $(C_7-C_{20})$arylalkyl, $C_7-C_{20}$ alkylaryl, $(C_6-C_{10})$aryloxy, $(C_1-C_{10})$fluoroalkyl, $(C_6-C_{10})$halogenoaryl, $(C_2-C_{10})$alkynyl; a radical —$SiR^6_3$, a halogen atom, or an aromatic radical having 5 or 6 ring members in the ring, at least one of which is a heteroatom, $R^5$ is hydrogen, $R^6$ is $(C_1-C_{10})$alkyl, $R^7$ is a radical

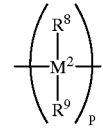

in which $M^2$ is carbon, silicon, germanium or tin, $R^8$ and $R^9$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or $R^8$ and $R^9$, together with the atom joining them form a ring, p is 1 or 3, and $R^{10}$ and $R^{11}$ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$arylalkenyl, hydroxyl or a halogen atom.

8. The catalyst as claimed in claim 7, wherein $M^1$ is zirconium, $R^{10}$ and $R^{11}$ are chlorine, $R^1$, $R^2$ and $R^3$ are identical or different and are hydrogen, $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen, or an aromatic radical having 5 or 6 ring members in the ring, at least one of which is a heteroatom, $R^4$ is $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen or an aromatic radical having 5 or 6 ring members in the ring, at least one of which is a heteroatom, and $M^2$ is silicon.

9. The catalyst as claimed in claim 8, wherein p is 1.

10. A catalyst comprising the combination which comprises:

(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine, and (b) a metallocene of the formula VI

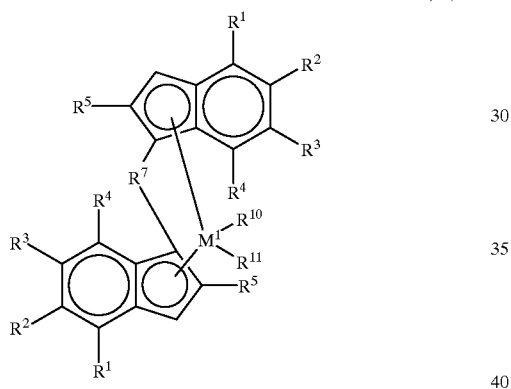

(VI)

in which $M^1$ is titanium, zirconium, hafnium, vanadium, niobium or tantalum, $R^1$, $R^2$ and $R^3$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$arylox, $(C_1-C_{10})$fluoroalkyl, $(C_6-C_{10})$halogenoaryl, $(C_2-C_{10})$alkynyl; a radical —$SiR^6_3$, a halogen atom, or an aromatic radical having 5 or 6 ring members in the ring, at least one of which is a heteroatom or adjacent radicals $R^1$—$R^4$ with the atoms joining them form a ring;

$R^4$ is $(C_1-C_{20})$alkyl, $(C_6-C_{14})$aryl, $(C_1-C_{10})$alkoxy, $(C_2-C_{10})$alkenyl, $(C_7-C_{20})$alylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl; a radical —$SiR^6_3$, a halogen atom, or an aromatic radical having 5 or 6 ring members in the ring, at least one of which is a heteroatom $R^5$ is a hydrogen, $R^6$ is $(C_1-C_{10})$alkyl, $R^7$ is a radical

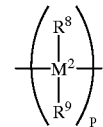

in which $M^2$ is silicon, germanium or tin, $R^8$ and $R^9$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or $R^8$ and $R^9$, together with the atom joining them form a ring, p is 1, 2 or 3, and $R^{10}$ and $R^{11}$ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$ arylalkenyl, hydroxyl or a halogen atom.

11. The catalyst as claimed in claim 10, wherein $M^1$ is zirconium, $R^{10}$ and $R^{11}$ are chlorine, $R^1$, $R^2$ and $R^3$ are identical or different and are hydrogen, $(C_1-C_{14})$alkyl, $(C_6-C_{14})$aryl, $(C_1-C_4)$alkoxy, $(C_2-C_6)$alkenyl, $(C_1-C_6)$fluoroalkyl, a halogen atom, or an aromatic radical having 5 or 6 ring members in the ring, at least one of which is a heteroatom, $R^4$ is $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen or an aromatic radical having 5 or 6 ring members in the ring, at least one of which is a heteroatom and $M^2$ is silicon.

12. A catalyst comprising the combination which comprises:

(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine, and (b) a metallocene of the formula VI

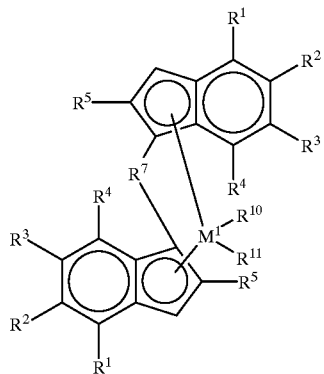
(VI)

in which
M$^1$ is titanium, zirconium, hafnium, vanadium, niobium or tantalum,
R$^1$, R$^2$ and R$^3$ are identical or different and are hydrogen, (C$_1$–C$_{20}$)alkyl, (C$_6$–C$_{14}$)aryl, (C$_1$–C$_{10}$)alkoxy, (C$_2$–C$_{10}$)alkenyl, (C$_7$–C$_{20}$)arylalkyl, (C$_7$–C$_{20}$)alkylaryl, (C$_6$–C$_{10}$)aryloxy, (C$_1$–C$_{10}$) fluoroalkyl, (C$_6$–C$_{10}$)halogenoaryl, (C$_2$–C$_{10}$) alkynyl; a radical —SiR$^6{}_3$, a halogen atom, or an aromatic radical having 5 or 6 ring members in the ring, at least one of which is a heteroatom or adjacent radicals R$^1$–R$^4$ with the atoms joining them form one or more rings;
R$^4$ is (C$_3$–C$_{20}$)alkyl, (C$_6$–C$_{14}$)aryl, (C$_4$–C$_{10}$)alkoxy, (C$_2$–C$_{10}$)alkenyl, (C$_7$–C$_{20}$)arylalkyl, (C$_7$–C$_{20}$) akylaryl, (C$_6$–C$_{10}$)aryloxy, (C$_1$–C$_{10}$)fluoroalkyl, (C$_6$–C$_{10}$)halogenoaryl, (C$_2$–C$_{10}$)alkynyl; a radical —SiR$^6{}_3$, a halogen atom, or an aromatic radical having 5 or 6 ring member in the ring, at least one of which is a heteroatom
R$^5$ is hydrogen,
R$^6$ is (C$_1$–C$_{10}$)alkyl,
R$^7$ is a radical

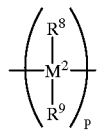

in which
M$^2$ is carbon, silicon, germanium or tin,
R$^8$ and R$^9$ are identical or different and are hydrogen, (C$_1$–C$_{20}$)alkyl, (C$_6$–C$_{14}$)aryl, (C$_1$–C$_{10}$)alkoxy, (C$_2$–C$_{10}$)alkenyl, (C$_7$–C$_{20}$)arylalkyl, (C$_7$–C$_{20}$) alkylaryl, (C$_6$–C$_{10}$)aryloxy, (C$_1$–C$_{10}$)fluoroalkyl, (C$_6$–C$_{10}$)halogenoaryl, (C$_2$–C$_{10}$)alkynyl or halogen or
R$^8$ and R$^9$, together with the atom joining them form a ring,
p is 1, 2 or 3, and
R$^{10}$ and R$^{11}$ are identical or different and are hydrogen, (C$_1$–C$_{10}$)alkyl, (C$_1$–C$_{10}$)alkoxy, (C$_6$–C$_{10}$)aryl, (C$_6$–C$_{10}$)aryloxy, (C$_2$–C$_{10}$)alkenyl, (C$_7$–C$_{40}$)arylalkyl, (C$_7$–C$_{40}$)alkylaryl, (C$_8$–C$_{40}$) arylalkenyl, hydroxyl or a halogen atom.
13. The catalyst as claimed in claim 12, wherein
M$^1$ is zirconium, R$^{10}$ and R$^{11}$ are chlorine,
R$^1$, R$^2$ and R$^3$ are identical or different and are hydrogen, (C$_1$–C$_{10}$)alkyl, (C$_6$–C$_{14}$)aryl, (C$_1$–C$_4$)alkoxy, (C$_2$–C$_6$) alkenyl, (C$_1$–C$_6$)fluoroalkyl, a halogen atom, or an aromatic radical having 5 or 6 ring members in the ring, at least one of which is a heteroatom,
R$^4$ is (C$_3$–C$_{10}$)alkyl, (C$_6$–C$_{14}$)aryl, (C$_4$–C$_{10}$)alkoxy, (C$_2$–C$_6$)alkenyl, (C$_1$–C$_6$)fluoroalkyl, a halogen atom, or an aromatic radical having 5 or 6 ring members in the ring, at least one of which is a heteroatom,
M$^2$ is silicon.
14. The catalyst as claimed in claim 13, wherein
R$^4$ is (C$_6$–C$_{14}$)aryl, (C$_2$–C$_6$)alkenyl, (C$_1$–C$_6$)fluoroakyl, a halogen or an aromatic radical having 5 or 6 ring members, and having at least one heteroatom.
15. A catalyst comprising the combination which comprises:
(a) an aluminoxane, a compound of the formula R$_x$NH$_{4-x}$BR'$_4$, R$_x$PH$_{4-x}$BR'$_4$, R$_3$CBR'$_4$ or BR'$_3$, or a mixture thereof, wherein X is an integer from 1 to 4 and the radicals R are identical or different and are a C$_1$–C$_{10}$-alkyl or a C$_6$–C$_{18}$-aryl or 2 radicals R together with the atom joining them form a ring, and the radicals R' are identical or different and are a C$_6$–C$_{18}$-aryl which optionally are substituted by alkyl, haloalkyl or fluorine, and
(b) a metallocene of the formula VI,

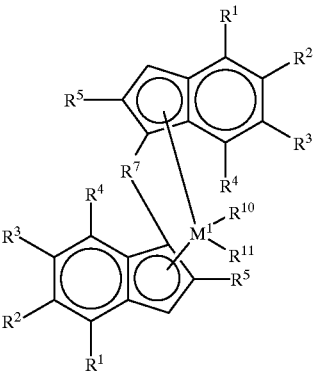
(VI)

in which
M$^1$ is titanium, zirconium, hafnium, vanadium, niobium or tantalum,
R$^1$, R$^2$ and R$^4$ are identical or different and are hydrogen; (C$_1$–C$_{20}$)alkyl, (C$_6$–C$_{14}$)aryl, (C$_1$–C$_{10}$)alkoxy, (C$_2$–C$_{10}$)alkenyl, (C$_7$–C$_{20}$)arylalkyl, (C$_7$–C$_{20}$) alkylaryl, (C$_6$–C$_{10}$)aryloxy, (C$_1$–C$_{10}$)fluoroalkyl, (C$_6$–C$_{10}$)halogenoaryl, (C$_2$–C$_{10}$)alkynyl; a radical —SiR$^6{}_3$, a halogen atom, or an aromatic radical having 5 or 6 ring members in the ring, at least one of which is a heteroatom or adjacent radicals R$^1$–R$^4$ with the atoms joining them form one or more rings,
R$^3$ is (C$_3$–C$_{20}$)alkyl, (C$_6$–C$_{14}$)aryl, (C$_4$–C$_{10}$)alkoxy, (C$_2$–C$_{10}$)alkenyl, (C$_7$–C$_{20}$)arylalkyl, (C$_7$–C$_{20}$) alkylaryl, (C$_6$–C$_{10}$)aryloxy, (C$_1$–C$_{10}$)fluoroalkyl, (C$_6$–C$_{10}$)halogenoaryl, (C$_2$–C$_{10}$)alkynyl; a radical —SiR$^6{}_3$, in which R$^6$ is (C$_1$–C$_{10}$)alkyl, a halogen atom, or an aromatic radical having 5 or 6 ring members in the ring, at least one of which is a heteroatom,
R$^5$ is hydrogen,
R$^6$ is (C$_1$–C$_{10}$)alkyl, R[7] is a radical $$\left(\begin{array}{c} R^8 \\ | \\ M^2 \\ | \\ R^9 \end{array}\right)_p$$

in which

M[2] is carbon, silicon, germanium or tin;

R[8] and R[9] are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or R[8] and R[9], together with the atom joining them form a ring, p is 1, 2 or 3, and R[10] and R[11] are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$arylalkenyl or hydroxyl.

16. The catalyst as claimed in claim 15 wherein

M[1] is zirconium,

R[1], R[2] and R[4] are identical or different and are hydrogen, $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen atom, or an aromatic radical having 5 or 6 ring members and can contain one or more heteroatoms, R[3] is $(C_3-C_{10})$alkyl, $(C_6-C_{14})$aryl, $C_4$-alkoxy, $(C_2-C_6)$alkenyl, $(C_1-C_6)$fluoroalkyl, a halogen atom, or an aromatic radical having 5 or 6 ring members in the ring, at least one of which is a heteroatom, and M[2] is silicon.

17. A catalyst comprising the combination which comprises:

(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine, and (b) a metallocene of the formula VI (VI)

in which

M[1] is titanium, zirconium, hafnium, vanadium, niobium or tantalum,

R[1], R[2] and R[4] are identical or different and are hydrogen; $(C_1-C_{20})$alkyl; $(C_6-C_{14})$aryl; $(C_1-C_{10})$alkoxy; $(C_2-C_{10})$alkenyl; $(C_7-C_{20})$arylalkyl; $(C_7-C_{20})$alkylaryl; $(C_6-C_{10})$aryloxy; $(C_1-C_{10})$fluoroalkyl; $(C_6-C_{10})$halogenoaryl; $(C_2-C_{10})$alkynyl; a radical —$SiR^6_3$, a halogen atom, or an aromatic radical having 5 or 6 ring members in the ring, at least one of which is a heteroatom or adjacent radicals R[1]–R[4] with the atoms joining them form one or more rings;

R[3] is $(C_1-C_{20})$alkyl; $(C_6-C_{14})$aryl; $(C_1-C_{10})$alkoxy; $(C_2-C_{10})$alkenyl; $(C_7-C_{20})$arylalkyl; $(C_7-C_{20})$alkylaryl; $(C_6-C_{10})$aryloxy; $(C_1-C_{10})$fluoroalkyl; $(C_6-C_{10})$halogenoaryl; $(C_2-C_{10})$alkynyl; a radical —$SiR^6_3$, a halogen atom, or an aromatic radical having 5 or 6 ring members in the ring, at least one of which is a heteroatom, R[5] is hydrogen, R[6] is $(C_1-C_{10})$alkyl, R[7] is a radical $$\left(\begin{array}{c} R^8 \\ | \\ M^2 \\ | \\ R^9 \end{array}\right)_p$$

in which

M[2] is carbon, silicon, germanium or tin;

R[8] is a $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen, R[9] is hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or $R^8$ and $R^9$, together with the atom joining them form a ring, p is 1, 2 or 3, and $R^{10}$ and $R^{11}$ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$arylalkenyl, hydroxyl or a halogen atom.

18. The catalyst as claimed in claim 17, wherein $M^1$ is zirconium, $R^{10}$ and $R^{11}$ are chlorine, $R^1$, $R^2$ and $R^4$ are identical or different and are hydrogen, $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen tom, or an aromatic radical having 5 or 6 ring members in the ring, at least one of which is a heteroatom, $R^3$ is $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen atom, or an aromatic radical having 5 or 6 ring members in the ring, at least one of which is a heteroatom, and $M^2$ is silicon.

19. The catalyst as claimed in claim 18, wherein $R^9$ is a $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen.

20. A catalyst comprising the combination which comprises:

(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine, and (b) a metallocene of the formula VI (VI)

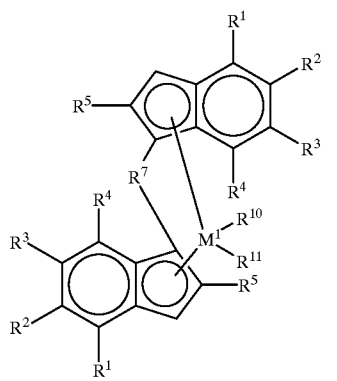

in which $M^1$ is titanium, zirconium, hafnium, vanadium, niobium or tantalum, $R^1$, $R^2$ and $R^4$ are identical or different and are hydrogen, $(C_1-C_{20})$alkyl; $(C_6-C_{14})$aryl; $(C_1-C_{10})$alkoxy; $(C_2-C_{10})$alkenyl; $(C_7-C_{20})$arylalkyl; $(C_7-C_{20})$alkylaryl; $(C_6-C_{10})$aryloxy; $(C_1-C_{10})$fluoroalkyl; $(C_6-C_{10})$halogenoaryl; $(C_2-C_{10})$alkynyl; a radical $-SiR^6_3$, a halogen atom, or an aromatic radical having 5 or 6 ring members in the ring, at least one of which is a heteroatom or adjacent radicals $R^1-R^4$ with the atoms joining them form one or more rings;

$R^3$ is $(C_1-C_{20})$alkyl; $(C_6-C_{14})$aryl; $(C_1-C_{10})$alkoxy; $(C_2-C_{10})$alkenyl; $(C_7-C_{20})$arylalkyl; $(C_7-C_{20})$alkylaryl; $(C_6-C_{10})$aryloxy; $(C_1-C_{10})$fluoroalkyl; $(C_6-C_{10})$halogenoaryl; $(C_2-C_{10})$alkynyl; a radical $-SiR^6_3$, a halogen atom, or an aromatic radical having 5 or 6 ring members in the ring, at least one of which is a heteroatom, $R^5$ is hydrogen, $R^6$ is $(C_1-C_{10})$alkyl, $R^7$ is a radical

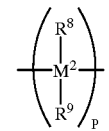

in which $M^2$ is carbon, silicon, germanium or tin, $R^8$ and $R^9$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or $R^8$ and $R^9$, together with the atom joining them form a ring, p is 1 or 3, and $R^{10}$ and $R^{11}$ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$arylalkenyl, hydroxyl or a halogen atom.

21. The catalyst as claimed in claim 20, wherein $M^1$ is zirconium, $R^{10}$ and $R^{11}$ are chlorine, $R^1$, $R^2$ and $R^4$ are identical or different and are hydrogen, $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen atom, or an aromatic radical having 5 or 6 ring members in the ring, at least one of which is a heteroatom, $R^3$ is $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen atom, or an aromatic radical having 5 or 6 ring members in the ring, at least one of which is a heteroatom, and $M^2$ is silicon.

22. The catalyst as claimed in claim 21, wherein p is 1.

23. A catalyst comprising the combination which comprises:

(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine, and (b) a metallocene of the formula VI

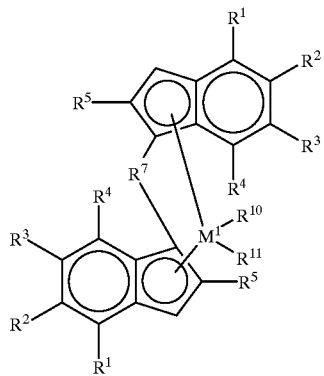

(VI)

in which
M¹ is titanium, zirconium, hafnium, vanadium, niobium or tantalum,
$R^1$, $R^2$ and $R^4$ are identical or different and are hydrogen; ($C_1$–$C_{20}$)alkyl; ($C_6$–$C_{14}$)aryl; ($C_1$–$C_{10}$)alkoxy; ($C_2$–$C_{10}$)alkenyl; ($C_7$–$C_{20}$)arylalkyl; ($C_7$–$C_{20}$)alkylaryl; ($C_6$–$C_{10}$)aryloxy; ($C_1$–$C_{10}$)flouroalkyl; ($C_6$–$C_{10}$)halogenoaryl; ($C_2$–$C_{10}$)alkynyl; a radical —$SiR^6_3$, a halogen atom, or an aromatic radical which having 5 or 6 ring members in the ring, at least one of which is a heteroatom or adjacent radicals $R^1$–$R^4$ with the atoms joining them form one or more rings; $R^3$ is ($C_1$–$C_{20}$)alkyl; ($C_6$–$C_{14}$)aryl; ($C_1$–$C_{10}$)alkoxy; ($C_2$–$C_{10}$)alkenyl; ($C_7$–$C_{20}$)arylalkyl, ($C_7$–$C_{20}$)alkylaryl; ($C_6$–$C_{10}$)aryloxy; ($C_1$–$C_{10}$)fluoroalkyl; ($C_6$–$C_{10}$)halogenoaryl; ($C_2$–$C_{10}$)alkynyl, a radical —$SiR^6_3$, a halogen atom, or an aromatic radical having 5 or 6 ring members in the ring, at least one of which is a heteroatom
$R^5$ is hydrogen,
$R^6$ is ($C_1$–$C_{10}$)alkyl,
$R^7$ is a radical

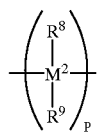

in which
M² is silicon, germanium or tin;
$R^8$ and $R^9$ are identical or different and are hydrogen, ($C_1$–$C_{20}$)alkyl, ($C_6$–$C_{14}$)aryl, ($C_1$–$C_{10}$)alkoxy, ($C_2$–$C_{10}$)alkenyl, ($C_7$–$C_{20}$)arylalkyl, ($C_7$–$C_{20}$)alkylaryl, ($C_6$–$C_{10}$)aryloxy, ($C_1$–$C_{10}$)fluoroalkyl, ($C_6$–$C_{10}$)halogenoaryl, ($C_2$–$C_{10}$)alkynyl or halogen or
$R^8$ and $R^9$, together with the atom joining them form a ring,
p is 1, 2 or 3, and
$R^{10}$ and $R^{11}$ are identical or different and are hydrogen, ($C_1$–$C_{10}$)alkyl, ($C_1$–$C_{10}$)alkoxy, ($C_6$–$C_{10}$)aryl, ($C_6$–$C_{10}$)aryloxy, ($C_2$–$C_{10}$)alkenyl, ($C_7$–$C_{40}$)arylalkyl, ($C_7$–$C_{40}$)alkylaryl, ($C_8$–$C_{40}$) arylalkenyl, hydroxyl or a halogen atom.

24. The catalyst as claimed in claim 23 wherein
M¹ is zirconium,
$R^{10}$ and $R^{11}$ are chlorine,
$R^1$, $R^2$ and $R^4$ are identical or different and are hydrogen, ($C_1$–$C_{10}$)alkyl, ($C_6$–$C_{14}$)aryl, ($C_1$–$C_4$)alkoxy, ($C_2$–$C_6$)alkenyl, ($C_1$–$C_6$)fluoroalkyl, a halogen atom, or an aromatic radical having 5 or 6 ring members in the ring, at least one of which is a heteroatom,
$R^3$ is ($C_1$–$C_{10}$)alkyl, ($C_6$–$C_{14}$)aryl, ($C_1$–$C_4$)alkoxy, ($C_2$–$C_6$)alkenyl, ($C_1$–$C_6$)fluoroalkyl, a halogen atom, or an aromatic radical having 5 or 6 ring members in the ring, at least one of which is a heteroatom, and
M² is silicon.

25. A catalyst comprising the combination which comprises:
(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1$–$C_{10}$-alkyl or a $C_6$–$C_{18}$-aryl or 2 radicals R together with the atom joining them form a ring, and the radicals R' are identical or different and are a $C_6$–$C_{18}$-aryl which optionally are substituted by alkyl, haloalkyl or fluorine, and
(b) a metallocene of the formula VI

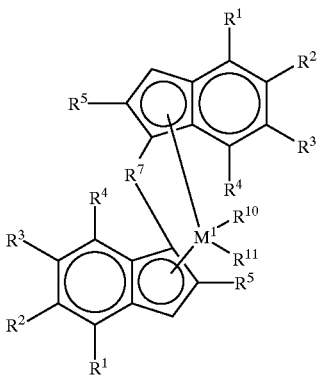

(VI)

in which
M¹ is titanium, zirconium, hafnium, vanadium, niobium or tantalum,
$R^1$, $R^2$ and $R^4$ are identical or different and are hydrogen; ($C_1$–$C_{20}$)alkyl, ($C_6$–$C_{14}$)aryl, ($C_1$–$C_{10}$)alkoxy, ($C_2$–$C_{10}$)alkenyl, ($C_7$–$C_{20}$)arylalkyl, ($C_7$–$C_{20}$)alkylaryl, ($C_6$–$C_{10}$)aryloxy, ($C_1$–$C_{10}$)fluoroalkyl, ($C_6$–$C_{10}$)halogenoaryl, ($C_2$–$C_{10}$)alkynyl; a radical —$SiR^6_3$, a halogen atom, or an aromatic radical having 5 or 6 ring members in the ring, at least one of which is a heteroatom or adjacent radicals $R^1$–$R^4$ with the atoms joining them form one or more rings,
$R^3$ is ($C_3$–$C_{20}$)alkyl, ($C_6$–$C_{14}$)aryl, ($C_1$–$C_{10}$)alkoxy, ($C_2$–$C_{10}$)alkenyl, ($C_7$–$C_{20}$)arylalkyl, ($C_7$–$C_{20}$)alkylaryl, ($C_6$–$C_{10}$)aryloxy, ($C_1$–$C_{10}$)fluoroalkyl, ($C_6$–$C_{10}$)halogenoaryl, ($C_2$–$C_{10}$)alkynyl; a radical —$SiR^6_3$, a halogen atom, or an aromatic radical having 5 or 6 ring members in the ring, at least one of which is a heteroatom,
$R^5$ is hydrogen,
$R^6$ is ($C_1$–$C_{10}$)alkyl, $R^7$ is a radical

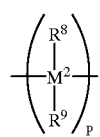

in which

M² is carbon, silicon, germanium or tin, $R^8$ and $R^9$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or $R^8$ and $R^9$, together with the atom joining them form a ring, p is 1, 2 or 3, and $R^{10}$ and $R^{11}$ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$arylalkenyl, hydroxyl or a halogen atom.

26. The catalyst as claimed in claim 25, wherein $M^1$ is zirconium, $R^{10}$ and $R^{11}$ are chlorine, $R^1$, $R^2$ and $R^4$ are identical or different and are hydrogen, $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen atom, or an aromatic radical having 5 or 6 ring members in the ring, at least one of which is a heteroatom $R^3$ is $(C_3-C_{10})$alkyl, $(C_6-C_{14})$aryl, $(C_1-C_4)$alkoxy, $(C_2-C_6)$alkenyl, $(C_1-C_6)$fluoroalkyl, a halogen atom, or an aromatic radical having 5 or 6 ring members in the ring, at least one of which is a heteroatom and $M^2$ is silicon.

27. The catalyst as claimed in claim 26 wherein $R^3$ is $(C_6-C_{14})$aryl, $(C_2-C_6)$alkenyl, $(C_1-C_6)$fluoroalkyl, a halogen or a radical having 5 or 6 ring members and containing at least one heteroatom.

28. A catalyst comprising the combination which comprises:

(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine, and (b) a metallocene of the formula VI

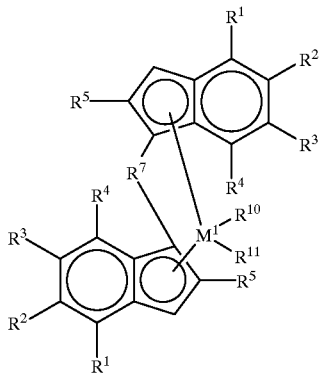

in which $M^1$ is titanium, zirconium, hafnium, vanadium, niobium or tantalum, $R^1$, $R^3$ and $R^4$ are identical or different and are hydrogen; $(C_1-C_{20})$alkyl; $(C_6-C_{14})$aryl; $(C_1-C_{10})$alkoxy; $(C_2-C_{10})$alkenyl; $(C_7-C_{20})$arylalkyl; $(C_7-C_{20})$alkylaryl; $(C_6-C_{10})$aryloxy; $(C_1-C_{10})$fluoroalkyl; $(C_6-C_{10})$halogenoaryl; $(C_2-C_{10})$alkynyl; a radical $—SiR^6_3$, a halogen atom; or an aromatic radical having 5 or 6 ring members in the ring, at lest one of which is a heteroatom or adjacent radicals $R^1$–$R^4$ with the atoms joining them form one or more rings;

$R^2$ is $(C_3-C_{20})$alkyl; $(C_6-C_{14})$aryl; $(C_4-C_{10})$alkoxy; $(C_2-C_{10})$alkenyl; $(C_7-C_{20})$arylalkyl; $(C_7-C_{20})$alkylaryl; $(C_6-C_{10})$aryloxy; $(C_1-C_{10})$fluoroalkyl; $(C_6-C_{10})$halogenoaryl; $(C_2-C_{10})$alkynyl; a radical $—SiR^6_3$, a halogen atom, or an aromatic radical having 5 or 6 ring members in the ring, at least one of which is a heteroatom, $R^5$ is hydrogen, $R^6$ is $(C_1-C_{10})$alkyl, $R^7$ is a radical

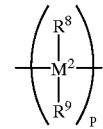

in which $M^2$ is carbon, silicon, germanium or tin, $R^8$ and $R^9$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or $R^8$ and $R^9$, together with the atom joining them form a ring, p is 1, 2 or 3, and $R^{10}$ and $R^{11}$ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$arylalkenyl, or hydroxyl.

29. The catalyst as claimed in claim 28, wherein $M^1$ is zirconium, $R^1$, $R^3$, and $R^4$ are identical or different and are hydrogen, $(C_1-C_{10})$alkyl, $(C_6-C_{14})$aryl, $(C_1-C_4)$alkoxy, $(C_2-C_6)$ alkenyl, $(C_1-C_6)$fluoroalkyl, a halogen atom, or an aromatic radical having 5 or 6 ring members in the ring, at least one of which is a heteroatom, $R^2$ is $(C_3-C_{10})$alkyl, $(C_6-C_{14})$aryl, $C_4$-alkoxy, $(C_2-C_6)$ alkenyl, $(C_1-C_6)$fluoroalkyl, a halogen atom or an aromatic radical having 5 or 6 ring members in the ring, at least one of which is a heteroatom, and $M^2$ is silicon.

30. A catalyst comprising the combination which comprises:

(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine, and (b) a metallocene of the formula VI

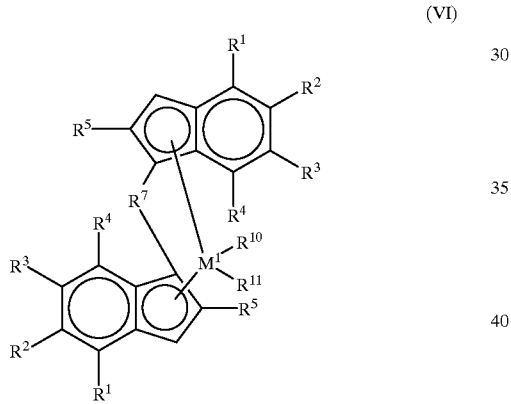

(VI)

in which $M^1$ is titanium, zirconium, hafnium, vanadium, niobium or tantalum, $R^1$, $R^3$ and $R^4$ are identical or different and are hydrogen, $(C_1-C_{20})$alkyl, $(C_6-C_{14})$aryl, $(C_1-C_{10})$ alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$ fluoroalkyl, $(C_6-C_{10})$halogenoaryl, $(C_2-C_{10})$ alkynyl, a radical —$SiR^6_3$, a halogen atom, or an aromatic radical having 5 or 6 ring members in the ring, at least one of which is a heteroatom, or adjacent radicals $R^1-R^4$ with the atoms joining them form one or more rings;

$R^2$ is $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$ alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6_3$, a halogen atom, or an aromatic radical having 5 or 6 ring members in the ring, at least one of which is a heteroatom, $R^5$ is hydrogen, $R^6$ is $(C_1-C_{10})$alkyl, $R^7$ is a radical

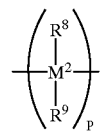

in which $M^2$ is carbon, silicon, germanium or tin, $R^8$ is $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$ alkylaryl, $(C_6-C_{10})$aryloxy, $(C_1-C_{10})$fluoroalkyl, $(C_6-C_{10})$halogenoaryl, $(C_2-C_{10})$alkynyl or halogen, $R^9$ is hydrogen, $(C_1-C_{20})$alkyl, $(C_6-C_{14})$aryl, $(C_1-C_{10})$alkoxy, $(C_2-C_{10})$alkenyl, $(C_7-C_{20})$ arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or $R^8$ and $R^9$, together with the atom joining them form a ring, p is 1, 2 or 3, and $R^{10}$ and $R^{11}$ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$ arylalkenyl, hydroxyl or a halogen atom.

31. The catalyst as claimed in claim 30, wherein $M^1$ is zirconium, $R^{10}$ and $R^{11}$ are chlorine, $R^1$, $R^3$, and $R^4$ are identical or different and are hydrogen, $(C_1-C_{10})$alkyl, $(C_6-C_{14})$aryl, $(C_1-C_4)$alkoxy, $(C_2-C_6)$ alkenyl, $(C_1-C_6)$fluoroalkyl, a halogen atom, or an aromatic radical having 5 or 6 ring members in the ring, at least one of which is a heteroatom, $R^2$ is $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen atom, or an aromatic radical having 5 or 6 ring members in the ring, at least one of which is a heteroatom, and $M^2$ is silicon.

32. The catalyst as claimed in claim 31, wherein $R^9$ is a $(C_1-C_{20})$alkyl, $(C_6-C_{14})$aryl, $(C_1-C_{10})$alkoxy, $(C_2-C_{10})$ alkenyl, $(C_7-C_{20})$arylalkyl, $(C_7-C_{20})$alkylaryl, $(C_6-C_{10})$ aryloxy, $(C_1-C_{10})$fluoroalkyl, $(C_6-C_{10})$halogenoaryl, $(C_2-C_{10})$alkynyl or halogen.

33. A catalyst comprising the combination which comprises:

(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine, and (b) a metallocene of the formula VI

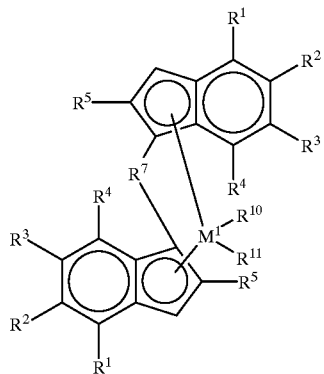

(VI)

in which
M$^1$ is titanium, zirconium, hafnium, vanadium, niobium or tantalum,
R$^1$, R$^3$ and R$^4$ are identical or different and are hydrogen, (C$_1$–C$_{20}$)alkyl, (C$_6$–C$_{14}$)aryl, (C$_1$–C$_{10}$)alkoxy, (C$_2$–C$_{10}$)alkenyl, (C$_7$–C$_{20}$)arylalkyl, (C$_7$–C$_{20}$)alkylaryl, (C$_6$–C$_{10}$)aryloxy, (C$_1$–C$_{10}$) fluoroalkyl, (C$_6$–C$_{10}$)halogenoaryl, (C$_2$–C$_{10}$) alkynyl, a radical —SiR$^6$$_3$, a halogen atom, or an aromatic radical having 5 or 6 ring members in the ring, at least one of which is a heteroatom, or adjacent radicals R$^1$–R$^4$ with the atoms joining them form one or more rings;
R$^2$ is (C$_1$–C$_{20}$)alkyl, (C$_6$–C$_{14}$)aryl, (C$_1$–C$_{10}$)alkoxy, (C$_2$–C$_{10}$)alkenyl, (C$_7$–C$_{20}$)arylalkyl, C$_7$–C$_{20}$) alkylaryl, (C$_6$–C$_{10}$)aryloxy, (C$_1$–C$_{10}$)fluoroalkyl, (C$_6$–C$_{10}$)halogenoaryl, (C$_2$–C$_{10}$)alkynyl radical —SiR$^6$$_3$, a halogen atom, or an aromatic radical having 5 or 6 ring members in the ring, at least one of which is a heteroatom
R$^5$ is hydrogen,
R$^6$ is (C$_1$–C$_{10}$)alkyl,
R$^7$ is a radical M$^2$

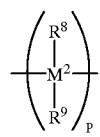

in which
M$^2$ is carbon, silicon, germanium or tin,
R$^8$ and R$^9$ are identical or different and are hydrogen, (C$_1$–C$_{20}$)alkyl, (C$_6$–C$_{14}$)aryl, (C$_1$–C$_{10}$)alkoxy, (C$_2$–C$_{10}$)alkenyl, (C$_7$–C$_{20}$)arylalkyl, (C$_7$–C$_{20}$) alkylaryl, (C$_6$–C$_{10}$)aryloxy, (C$_1$–C$_{10}$)fluoroalkyl, (C$_6$–C$_{10}$)halogenoaryl, (C$_2$–C$_{10}$)alkynyl or halogen or R$^8$ and R$^9$, together with the atom joining them form a ring,
p is 1 or 3, and
R$^{10}$ and R$^{11}$ are identical or different and are hydrogen, (C$_1$–C$_{10}$)alkyl, (C$_1$–C$_{10}$)alkoxy, (C$_6$–C$_{10}$)aryl, (C$_6$–C$_{10}$)aryloxy, (C$_2$–C$_{10}$)alkenyl, (C$_7$–C$_{40}$)arylalkyl, (C$_7$–C$_{40}$)alkylaryl, (C$_8$–C$_{40}$) arylalkenyl, hydroxyl or a halogen atom.

34. The catalyst as claimed in claim 33, wherein M$^1$ is zirconium,
R$^{10}$ and R$^{11}$ are chlorine, R$^1$, R$^3$, and R$^4$ are identical or different and are hydrogen, (C$_1$–C$_{10}$)alkyl, (C$_6$–C$_{14}$)aryl, (C$_1$–C$_4$)alkoxy, (C$_2$–C$_6$) alkenyl, (C$_1$–C$_6$)fluoroalkyl, a halogen atom, or an aromatic radical having 5 or 6 ring members in the ring, at least one of which is a heteroatom,
R$^2$ is (C$_1$–C$_{10}$)alkyl, (C$_6$–C$_{14}$)aryl, (C$_1$–C$_4$)alkoxy, (C$_2$–C$_6$)alkenyl, (C$_1$–C$_6$)fluoroalkyl, a halogen atom, or an aromatic radical having 5 or 6 ring members in the ring, at least one of which is a heteroatom, and
M$^2$ is silicon.

35. The catalyst as claimed in claimed 34, wherein p is 1.
36. A catalyst comprising the combination which comprises:
(a) an aluminoxane, a compound of the formula R$_x$NH$_{4-x}$BR'$_4$, R$_x$PH$_{4-x}$BR'$_4$, R$_3$CBR'$_4$ or BR'$_3$, or a mixture thereof, wherein X is an integer from 1 to 4 and the radicals R are identical or different and are a C$_1$–C$_{10}$-alkyl or a C$_6$–C$_{18}$-aryl or 2 radicals R together with the atom joining them form a ring, and the radicals R' are identical or different and are a C$_6$–C$_{18}$-aryl which optionally are substituted by alkyl, haloalkyl or fluorine, and
(b) a metallocene of the formula VI

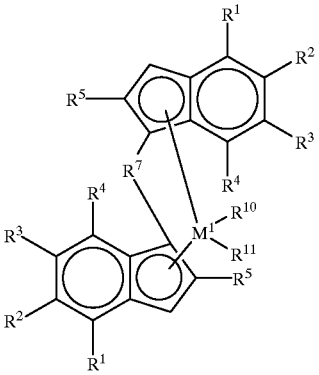

(VI)

in which
M$^1$ is titanium, zirconium, hafnium, vanadium, niobium or tantalum,
R$^1$, R$^3$ and R$^4$ are identical or different and are hydrogen, (C$_1$–C$_{20}$)alkyl, (C$_6$–C$_{14}$)aryl, (C$_1$–C$_{10}$) alkoxy, (C$_2$–C$_{10}$)alkenyl, (C$_7$–C$_{20}$)arylalkyl, (C$_7$–C$_{20}$)alkylaryl, (C$_6$–C$_{10}$)aryloxy, (C$_1$–C$_{10}$) fluoroalkyl, (C$_6$–C$_{10}$)halogenoaryl, (C$_2$–C$_{10}$) alkynyl, a radical —SiR$^6$$_3$, a halogen atom, or an aromatic radical having 5 or 6 ring members in the ring, at least one of which is a heteroatom or adjacent radicals R$^1$–R$^4$ with the atoms joining them form one or more rings;
R$^2$ is (C$_1$–C$_{20}$)alkyl, (C$_6$–C$_{14}$)aryl, (C$_1$–C$_{10}$)alkoxy, (C$_2$–C$_{10}$)alkenyl, (C$_7$–C$_{20}$)alkylaryl, (C$_7$–C$_{20}$) alkylaryl, (C$_6$–C$_{10}$)aryloxy, (C$_1$–C$_{10}$)fluoroalkyl, (C$_6$–C$_{10}$)halogenoaryl, (C$_2$–C$_{10}$)alkynyl, a radical —SiR$^6$$_3$, a halogen atom, or an aromatic radical having 5 or 6 ring members in the ring, at least one of which is a heteroatom,
R$^5$ is hydrogen,
R$^6$ is (C$_1$–C$_{10}$)alkyl, $R^7$ is a radical

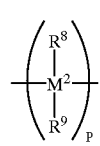

in which

M² is silicon, germanium or tin, $R^8$ and $R^9$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or $R^8$ and $R^9$, together with the atom joining them form a ring, p is 1, 2 or 3, and $R^{10}$ and $R^{11}$ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$arylalkenyl, hydroxyl or a halogen atom.

37. The catalyst as claimed in claim 36, wherein $M^1$ is zirconium, $R^{10}$ and $R^{11}$ are chlorine, $R^1$, $R^3$, and $R^4$ are identical or different and are hydrogen, $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen or an aromatic radical having 5 or 6 ring members in the ring, at least one of which is a heteroatom, $R^2$ is $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen or an aromatic radical having 5 or 6 ring members and can contain one or more heteroatoms, and $M^2$ is silicon.

38. A catalyst comprising the combination which comprises:

(a) an aluminoxane, a compound of the formula $R_xNH_{4-x}BR'_4$, $R_xPH_{4-x}BR'_{4-x}$, $R_3CBR'_4$ or $BR'_3$, or a mixture thereof, wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine, and (b) a metallocene of the formula VI

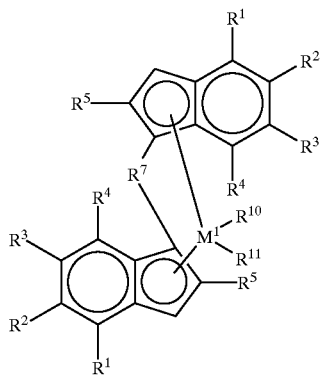

in which $M^1$ is titanium, zirconium, hafnium, vanadium, niobium or tantalum, $R^1$, $R^3$ and $R^4$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluroalkyl, $(C_6-C_{10})$halogenoaryl, $(C_2-C_{10})$alkynyl; a radical —$SiR^6_3$, a halogen atom, or an aromatic radical having 5 or 6 ring members in the ring, at least are of which is a heteroatom or adjacent radicals $R^1-R^4$ with the atoms joining them form one or more rings;

$R^2$ is $(C_3-C_{20})$alkyl, $(C_6-C_{14})$aryl; $(C_4-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6_3$, a halogen atom, or an aromatic radical having 5 or 6 ring members in the ring, at least one of which is a heteroatom, $R^5$ is hydrogen, $R^6$ is $(C_1-C_{10})$alkyl, $R^7$ is a radical

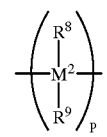

in which $M^2$ is carbon, silicon, germanium or tin;

$R^8$ and $R^9$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or $R^8$ and $R^9$, together with the atom joining them form a ring, p is 1, 2 or 3, and $R^{10}$ and $R^{11}$ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$arylalkenyl, hydroxyl or a halogen atom.

39. The catalyst as claimed in claim 38 wherein
M$^1$ is zirconium,
R$^{10}$ and R$^{11}$ are chlorine,
R$^1$, R$^3$, and R$^4$ are identical or different and are hydrogen, (C$_1$–C$_{10}$)alkyl, (C$_6$–C$_{14}$)aryl, (C$_1$–C$_4$)alkoxy, (C$_2$–C$_6$)alkenyl, (C$_1$–C$_6$)fluoroalkyl, a halogen or an aromatic radical having 5 or 6 ring members in the ring, at least one of which is a heteroatom or adjacent radicals R$^1$–R$^4$ with the atoms joining them form a ring,
R$^2$ is (C$_3$–C$_{10}$)alkyl, (C$_6$–C$_{14}$)aryl, (C$_4$–C$_{10}$)alkoxy, (C$_2$–C$_6$)alkenyl, (C$_1$–C$_6$)fluoroalkyl, a halogen or an aromatic radical having 5 or 6 ring members in the ring, at least one of which is a heteroatom, and
M$^2$ is silicon.

40. The catalyst as claimed in claim 39, wherein R$^2$ is (C$_6$–C$_{14}$)aryl, (C$_2$–C$_6$)alkenyl, (C$_1$–C$_6$)fluoroalkyl, a halogen atom, or an aromatic radical having 5 or 6 ring members in the ring, at least one of which is a heteroatom.

41. A catalyst comprising the combination of components which comprises:
(a) an aluminoxane, a compound of the formula R$_x$NH$_{4-x}$BR'$_4$, R$_x$PH$_{4-x}$BR'$_4$, R$_3$CBR'$_4$ or BR'$_3$, or a mixture thereof, wherein X is an integer from 1 to 4 and the radicals R are identical or different and are a C$_1$–C$_{10}$-alkyl or a C$_6$–C$_{18}$-aryl or 2 radicals R together with the atom joining them form a ring, and the radicals R' are identical or different and are a C$_6$–C$_{18}$-aryl which optionally are substituted by alkyl, haloalkyl or fluorine, and
(b) a metallocene of the formula VI (VI)

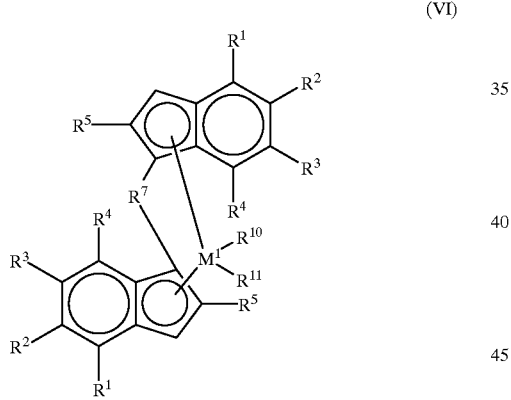

in which
M$^1$ is titanium, zirconium, hafnium, vanadium, niobium or tantalum,
R$^1$ is (C$_3$–C$_{20}$)alkyl, (C$_6$–C$_{14}$)aryl, (C$_4$–C$_{10}$)alkoxy, (C$_2$–C$_{10}$)alkenyl, (C$_7$–C$_{20}$)arylalkyl, (C$_7$–C$_{20}$)alkylaryl, (C$_6$–C$_{10}$)aryloxy, (C$_1$–C$_{10}$)fluoroalkyl, (C$_6$–C$_{10}$)halogenoaryl, (C$_2$–C$_{10}$)alkynyl, a radical —SiR$^6_3$, a halogen atom, or an aromatic radical having 5 or 6 members in the ring, at least one of which is a heteroatom,
R$^2$, R$^3$ and R$^4$ are identical or different and are hydrogen, (C$_1$–C$_{20}$)alkyl, (C$_6$–C$_{14}$)aryl, (C$_1$–C$_{10}$) alkoxy, (C$_2$–C$_{10}$)alkenyl, (C$_7$–C$_{20}$)arylalkyl, (C$_7$–C$_{20}$)alkylaryl, (C$_6$–C$_{10}$)aryloxy, (C$_1$–C$_{10}$)fluoroalkyl, (C$_6$–C$_{10}$)halogenoaryl, (C$_2$–C$_{10}$)alkynyl, a radical —SiR$^6_3$, a halogen atom, or an aromatic radical having 5 or 6 ring members in the ring, at least one of which is a herteroatom or adjacent radicals R$^1$–R$^4$ with the atoms joining them form one or more rings;
R$^5$ is hydrogen,
R$^6$ is (C$_1$–C$_{10}$)alkyl,
R$^7$ is a radical

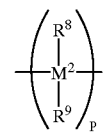

in which
M$^2$ is carbon, silicon, germanium or tin;
R$^8$ and R$^9$ are identical or different and are hydrogen, (C$_1$–C$_{20}$)alkyl, (C$_6$–C$_{14}$)aryl, (C$_1$–C$_{10}$)alkoxy, (C$_2$–C$_{10}$)alkenyl, (C$_7$–C$_{20}$)arylalkyl, (C$_7$–C$_{20}$)alkylaryl, (C$_6$–C$_{10}$)aryloxy, (C$_1$–C$_{10}$)fluoroalkyl, (C$_6$–C$_{10}$)halogenoaryl, (C$_2$–C$_{10}$)alkynyl or halogen or
R$^8$ and R$^9$, together with the atom joining them form a ring,
p is 1, 2 or 3, and
R$^{10}$ and R$^{11}$ are identical or different and are hydrogen, (C$_1$–C$_{10}$)alkyl, (C$_1$–C$_{10}$)alkoxy, (C$_6$–C$_{10}$)aryl, (C$_6$–C$_{10}$)aryloxy, (C$_2$–C$_{10}$)alkenyl, (C$_7$–C$_{40}$)arylalkyl, (C$_7$–C$_{40}$)alkylaryl, (C$_8$–C$_{40}$) arylalkenyl, or hydroxyl.

42. The catalyst as claimed in claim 41, wherein
M$^1$ is zirconium,
R$^1$ is (C$_3$–C$_{10}$)alkyl, (C$_6$–C$_{14}$)aryl, C$_4$-alkoxy, (C$_2$–C$_6$)alkenyl, (C$_1$–C$_6$)fluoroalkyl, a halogen or an aromatic radical having 5 or 6 ring members and can contain one or more heteroatoms,
R$^2$, R$^3$ and R$^4$ are identical or different and are hydrogen, (C$_1$–C$_{10}$)alkyl, (C$_6$–C$_{14}$)aryl, (C$_1$–C$_4$)alkoxy, (C$_2$–C$_6$)alkenyl, (C$_1$–C$_6$)fluoroalkyl, a halogen or an aromatic radical having 5 or 6 ring members in the ring, at least one of which is a heteroatom and
M$^2$ is silicon.

43. A catalyst comprising the combination of components which comprises:
(a) an aluminoxane, a compound of the formula R$_x$NH$_{4-x}$BR'$_4$, R$_x$PH$_{4-x}$BR'$_4$, R$_3$CBR'$_4$ or BR'$_3$, or a mixture thereof, wherein X is an integer from 1 to 4 and the radicals R are identical or different and are a C$_1$–C$_{10}$-alkyl or a C$_6$–C$_{18}$-aryl or 2 radicals R together with the atom joining them form a ring, and the radicals R' are identical or different and are a C$_6$–C$_{18}$-aryl which optionally are substituted by alkyl, haloalkyl or fluorine, and (b) a metallocene of the formula VI

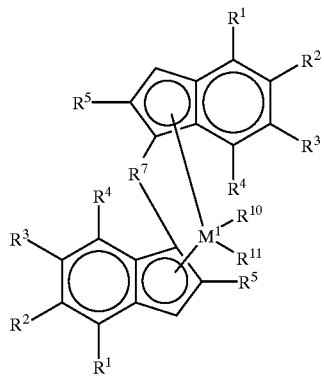
(VI)

in which
M¹ is titanium, zirconium, hafnium, vanadium, niobium or tantalum,
R¹ is $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl; a radical —$SiR^6_3$, a halogen atom, or an aromatic radical having 5 or 6 ring members in the ring, at least one of which is a heteroatom,
$R^2$, $R^3$ and $R^4$ are identical or different and are hydrogen; $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl; a radical —$SiR^6_3$, a halogen atom, or an aromatic radical having 5 or 6 ring members and can contain one or more heteroatoms, or adjacent radicals $R^1-R^4$ with the atoms joining them form one or more rings;
$R^5$ is hydrogen,
$R^6$ is $(C_1-C_{10})$alkyl,
$R^7$ is a radical

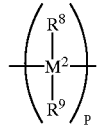

in which
M² is carbon, silicon, germanium or tin;
$R^8$ is $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, or halogen,
$R^9$ is hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, or halogen, or
$R^8$ and $R^9$, together with the atom joining them form a ring,
p is 1, 2 or 3, and
$R^{10}$ and $R^{11}$ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$arylalkenyl, hydroxyl or a halogen atom.

44. The catalyst as claimed in claim 43, wherein
M¹ is zirconium,
$R^{10}$ and $R^{11}$ are chlorine,
R¹ is $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen atom, or an aromatic radical having 5 or 6 ring members in the ring, at least one of which is a herteroatom,
$R^2$, $R^3$ and $R^4$ are identical or different and are hydrogen, $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen atom, or an aromatic radical having 5 or 6 ring members in the ring, at least one of which is a herteroatom and
M² is silicon.

45. The catalyst as claimed in claim 44, wherein $R^9$ is $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen.

46. A catalyst comprising the combination of components which comprises:
(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine, and
(b) a metallocene of the formula VI

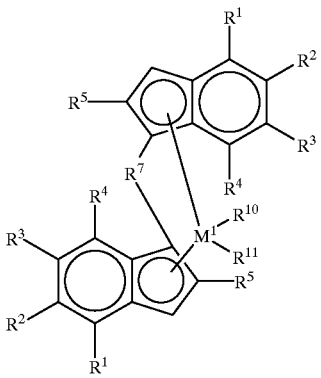
(VI)

in which
M¹ is titanium, zirconium, hafnium, vanadium, niobium or tantalum,
R¹ is $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6_3$, a halogen atom, or an aromatic radical having 5 or 6 ring members in the ring, at least one of which is a heteroatom,
$R^2$, $R^3$ and $R^4$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl; a radical —$SiR^6_3$, a halogen atom, or an aromatic radical having 5 or 6 ring members in the ring, at least one of which is a heteroatom, or adjacent radicals $R^1$–$R^4$ with the atoms joining them form one or more rings;

$R^5$ is hydrogen, $R^6$ is $(C_1$–$C_{10})$alkyl, $R^7$ is a radical

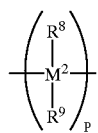

in which $M^2$ is carbon, silicon, germanium or tin;

$R^8$ and $R^9$ are identical or different and are hydrogen, $(C_1$–$C_{20})$alkyl, $(C_6$–$C_{14})$aryl, $(C_1$–$C_{10})$alkoxy, $(C_2$–$C_{10})$alkenyl, $(C_7$–$C_{20})$arylalkyl, $(C_7$–$C_{20})$ alkylaryl, $(C_6$–$C_{10})$aryloxy, $(C_1$–$C_{10})$fluoroalkyl, $(C_6$–$C_{10})$halogenoaryl, $(C_2$–$C_{10})$alkynyl or halogen or $R^8$ and $R^9$, together with the atom joining them form a ring, p is 1 or 3, and $R^{10}$ and $R^{11}$ are identical or different and are hydrogen, $(C_1$–$C_{10})$alkyl, $(C_1$–$C_{10})$alkoxy, $(C_6$–$C_{10})$aryl, $(C_6$–$C_{10})$aryloxy, $(C_2$–$C_{10})$alkenyl, $(C_7$–$C_{40})$arylalkyl, $(C_7$–$C_{40})$alkylaryl, $(C_8$–$C_{40})$ arylalkenyl, hydroxyl or a halogen atom.

47. The catalyst as claimed in claim 46, wherein $M^1$ is zirconium, $R^{10}$ and $R^{11}$ are chlorine, $R^1$ is $(C_1$–$C_{10})$alkyl, $(C_6$–$C_{14})$aryl, $(C_1$–$C_4)$alkoxy, $(C_2$–$C_6)$alkenyl, $(C_1$–$C_6)$fluoroalkyl, a halogen atom, or an aromatic radical having 5 or 6 ring members in the ring, at least one of which is a heteroatom, $R^2$, $R^3$ and $R^4$ are identical or different and are hydrogen, $(C_1$–$C_{10})$alkyl, $(C_6$–$C_{14})$aryl, $(C_1$–$C_4)$alkoxy, $(C_2$–$C_6)$ alkenyl, $(C_1$–$C_6)$fluoroalkyl, a halogen atom, or an aromatic radical having 5 or 6 ring members in the ring, at least one of which is a heteroatom, and $M^2$ is silicon.

48. The catalyst as claimed in claim 47, wherein p is 1.

49. A catalyst comprising the combination of components which comprises:

(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1$–$C_{10}$-alkyl or a $C_6$–$C_{18}$-aryl or 2 radicals R together with the atom joining them form a ring, and the radicals R' are identical or different and are a $C_6$–$C_{18}$-aryl which optionally are substituted by alkyl, haloalkyl or fluorine, and b) a metallocene of the formula VI

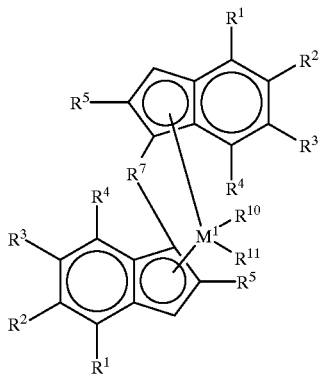

(VI)

in which $M^1$ is titanium, zirconium, hafnium, vanadium, niobium or tantalum, $R^1$ is $(C_1$–$C_{20})$alkyl, $(C_6$–$C_{14})$aryl, $(C_1$–$C_{10})$alkoxy, $(C_2$–$C_{10})$alkenyl, $(C_7$–$C_{20})$arylalkyl, $(C_7$–$C_{20})$ alkylaryl, $(C_6$–$C_{10})$aryloxy, $(C_1$–$C_{10})$fluoroalkyl, $(C_6$–$C_{10})$halogenoaryl, $(C_2$–$C_{10})$alkynyl; a radical —$SiR^6_3$, a halogen atom, or an aromatic radical having 5 or 6 ring members in the ring, at least one of which is a heteroatom, $R^2$, $R^3$ and $R^4$ are identical or different and are hydrogen, $(C_1$–$C_{20})$alkyl, $(C_6$–$C_{14})$aryl, $(C_1$–$C_{10})$ alkoxy, $(C_2$–$C_{10})$alkenyl, $(C_7$–$C_{20})$arylalkyl, $(C_7$–$C_{20})$alkylaryl, $(C_6$–$C_{10})$aryloxy, $(C_1$–$C_{10})$ fluoroalkyl, $(C_6$–$C_{10})$halogenoaryl, $(C_2$–$C_{10})$ alkynyl, a radical —$SiR^6_3$, a halogen atom, or an aromatic radical having 5 or 6 ring members in the ring, at least one of which is a heteroatom, or adjacent radicals $R^1$–$R^4$ with the atoms joining them form one or more rings;

$R^5$ is hydrogen, $R^6$ is $(C_1$–$C_{10})$alkyl, $R^7$ is a radical

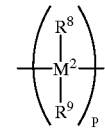

in which $M^2$ is silicon, germanium or tin;

$R^8$ and $R^9$ are identical or different and are hydrogen, $(C_1$–$C_{20})$alkyl, $(C_6$–$C_{14})$aryl, $(C_1$–$C_{10})$alkoxy, $(C_2$–$C_{10})$alkenyl, $(C_7$–$C_{20})$arylalkyl, $(C_7$–$C_{20})$ alkylaryl, $(C_6$–$C_{10})$aryl, $(C_1$–$C_{10})$fluoroalkyl, $(C_6$–$C_{10})$halogenoaryl, $(C_2$–$C_{10})$alkynyl or halogen or $R^8$ and $R^9$, together with the atom joining them form a ring, p is 1, 2 or 3, and $R^{10}$ and $R^{11}$ are identical or different and are hydrogen, $(C_1$–$C_{10})$alkyl, $(C_1$–$C_{10})$alkoxy, $(C_6$–$C_{10})$aryl, $(C_6$–$C_{10})$aryloxy, $(C_2$–$C_{10})$alkenyl, $(C_7$–$C_{40})$arylalkyl, $(C_7$–$C_{40})$, $(C$–$C_{40})$arylalkenyl, hydroxyl or a halogen atom.

50. The catalyst as claimed in claim 49, wherein $M^1$ is zirconium, $R^{10}$ and $R^{11}$ are chlorine, $R^1$ is $(C_1-C_{10})$alkyl, $(C_6-C_4)$aryl, $(C_1-C_4)$alkoxy, $(C_2-C_6)$alkenyl, $(C_1-C_6)$fluoroalkyl, a halogen atom, or an aromatic radical having 5 or 6 ring members in the ring, at least one of which is a heteroatom, $R^2$, $R^3$ and $R^4$ are identical or different and are hydrogen, $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen atom, or an aromatic radical having 5 or 6 ring members in the ring, at least one of which is a heteroatom, and $M^2$ is silicon.

51. A catalyst comprising the combination of components which comprises:

(a) an aluminoxane, a compound of the formula $R_xNH_{4-x}BR'_4$, $R_xPH_{4-x}BR'_4$, $R_3CBR'_4$ or $BR'_3$, or a mixture thereof, wherein X is an integer from 1 to 4 and the radicals R are identical or different and are a $C_1-C_{10}$-alkyl or a $C_6-C_{18}$-aryl or 2 radicals R together with the atom joining them from a ring, and the radicals R' are identical or different and are a $C_6-C_{18}$-aryl which optionally are substituted by alkyl, haloalkyl or fluorine, and (b) a metallocene of the formula VI

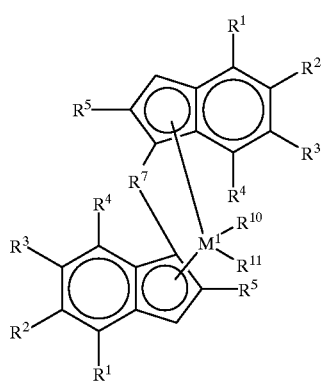

(VI)

in which $M^1$ is titanium, zirconium, hafnium, vanadium, niobium or tantalum, $R^1$ is $(C_3-C_{20})$alkyl, $(C_6-C_{14})$aryl, $(C_4-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl; a radical —$SiR^6_3$, a halogen atom; or an aromatic radical having 5 or 6 ring members in the ring, at least one of which is a heteroatom, $R^2$, $R^3$ and $R^4$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6_3$, a halogen atom, or an aromatic radical having 5 or 6 ring members in the ring, at least one of which is a heteroatom, or adjacent radicals $R^1-R^4$ with the atoms joining them form one or more rings;

$R^5$ is hydrogen, $R^6$ is $(C_1-C_{10})$alkyl, $R^7$ is a radical

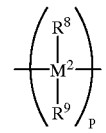

in which $M^2$ is carbon, silicon, germanium or tin;

$R^8$ and $R^9$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or $R^8$ and $R^9$, together with the atom joining them, form a ring, p is 1, 2 or 3; and $R^{10}$ and $R^{11}$ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$ arylalkenyl, hydroxyl or a halogen atom.

52. The catalyst as claimed in claim 51, wherein $M^1$ is zirconium, $R^{10}$ and $R^{11}$ are chlorine, $R^1$ is $(C_3-C_{10})$alkyl, $(C_6-C_{14})$aryl, $(C_4-C_{10})$alkoxy, $(C_2-C_6)$alkenyl, $(C_1-C_6)$fluoroalkyl, a halogen atom, or an aromatic radical having 5 or 6 ring members in the ring, at least one of which is a heteroatom, $R^2$, $R^3$ and $R^4$ are identical or different and are hydrogen, $(C_1-C_{10})$alkyl, $(C_6-C_{14})$aryl, $(C_1-C_4)$alkoxy, $(C_2-C_6)$ alkenyl, $(C_1-C_6)$fluoroalkyl, a halogen atom, or an aromatic radical having 5 or 6 ring members in the ring, at least one of which is a heteroatom, and $M^2$ is silicon.

53. The catalyst as claimed in claim 52, wherein $R^1$ is $(C_6-C_{14})$aryl, $(C_2-C_6)$alkenyl, $(C_1-C_6)$fluoroalkyl, a halogen or an aromatic radical having 5 or 6 ring members in the ring, at least one of which is a heteroatom.

54. A catalyst comprising the combination of components which comprises:

(a) an aluminoxane, a compound of the formula $R_xNH_{4-x}BR'_4$, $R_xPH_4$, $BR'_4$, $R_3CBR'_4$ or $BR'_3$ or a mixture thereof wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine, and (b) a metallocene of the formula VI

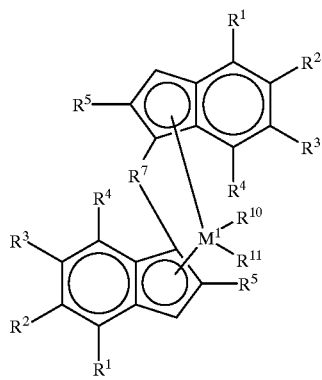

(VI)

in which
- $M^1$ is titanium, zirconium, hafnium, vanadium, niobium or tantalum,
- $R^1$, $R^2$, $R^3$, and $R^4$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $C_6-C_{10}$aryloxy, $(C_1-C_{10})$fluoroalkyl, $(C_6-C_{10})$halogenoaryl, $(C_2-C_{10})$alkynyl, a radical —$SiR^6{}_3$, a halogen atom, or an aromatic radical having 5 or 6 ring members in the ring, at least one of which is a heteroatom or adjacent radicals $R^1$–$R^4$ with the atoms joining them form one or more rings;
- $R^5$ is $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6{}_3$, a halogen atom or an aromatic radical having 5 or 6 ring members in the ring, at least one of which is a heteroatom,
- $R^6$ is $(C_1-C_{10})$alkyl,
- $R^7$ is a radical

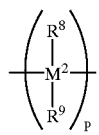

in which p is 0 and the metallocene is unbridged, and $R^{10}$ and $R^{11}$ are identical or different and are hydrogen, $(C_1-C_{10})$alkyl, $(C_1-C_{10})$alkoxy, $(C_6-C_{10})$aryl, $(C_6-C_{10})$aryloxy, $(C_2-C_{10})$alkenyl, $(C_7-C_{40})$arylalkyl, $(C_7-C_{40})$alkylaryl, $(C_8-C_{40})$arylalkenyl, hydroxyl or a halogen atom.

55. The catalyst as claimed in claim 54, wherein
- $M^1$ is zirconium,
- $R^{10}$ and $R^{11}$ are chlorine,
- $R^1$, $R^2$, $R^3$ and $R^4$ are identical or different and are hydrogen, $(C_1-C_{10})$alkyl, $(C_6-C_{14})$aryl, $(C_1-C_4)$alkoxy, $(C_2-C_6)$alkenyl, $(C_1-C_6)$fluoroalkyl, a halogen or a hetero-aromatic radical which has 5 or 6 ring members and optionally contains one or more heteroatoms or adjacent radicals $R^1$–$R^4$, with the atoms joining them form a ring,
- $R^5$ is $(C_1-C_{10})$alkyl, and
- $M^2$ is silicon.

56. The catalyst as claimed in claim 55, wherein $R^1$–$R^4$ with the atoms joining them form one or more rings.

57. A catalyst comprising the combination of the components which comprises:

(a) an aluminoxane, a compound of the formula $R_xNH_{4-x}BR'_4$, $R_xPH_{4-x}BR'_4$, $R_3CBR'_4$ or $BR'_3$ or a mixture thereof, wherein X is an integer from 1 to 4 and the radicals R are identical or different and are a $C_1-C_{10}$-alkyl or a $C_6-C_{18}$-aryl or 2 radicals R together with the atom joining them form a ring, and the radicals R' are identical or different and are a $C_6-C_{18}$-aryl which optionally are substituted by alkyl, haloalkyl or fluorine; and (b) a metallocene of the formula VI

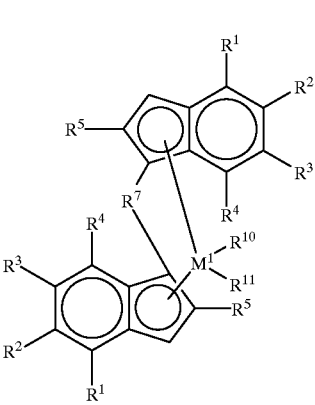

(VI)

in which
- $M^1$ is titanium, zirconium, hafnium, vanadium, niobium or tantalum, $R^1$, $R^2$, $R^3$, $R^4$ and $R^5$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl, a radical —$SiR^6{}_3$, a halogen atom, or an aromatic radical having 5 or 6 ring members in the ring, at least one of which is a heteroatom, or adjacent radicals $R^1$–$R^4$ with the atoms joining them form one or more rings;
- $R^6$ is $(C_1-C_{10})$alkyl;
- $R^7$ is a radical

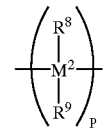

in which
- $M^2$ is carbon, silicon, germanium or tin;
- $R^8$ and $R^9$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$halogenoaryl, $(C_2-C_{10})$alkynyl or halogen or
- $R^8$ and $R^9$, together with the atom joining them form a ring
- p is 0, 1, 2 or 3; and
- $R^{10}$ and $R^{11}$ are identical or different and are hydrogen, $(C_1-C_{10})$alkyl, $(C_1-C_{10})$alkoxy, ($C_6$–$C_{10}$)aryl, ($C_6$–$C_{10}$)aryloxy, ($C_2$–$C_{10}$)alkenyl, ($C_7$–$C_{40}$)arylalkyl, ($C_7$–$C_{40}$)alkylaryl, ($C_8$–$C_{40}$)arylalkenyl, hydroxyl or a halogen atom, and the indenyl radicals in formula VI are substituted by non-hydrogen substituents in the 2,4,6-; 2,4,5-; 2,4,5,6- or 2,4,5,6,7-position.

58. The catalyst as claimed in claim 57, wherein $M^1$ is zirconium, $R^{10}$ and $R^{11}$ are chlorine and said aluminoxane is methyl aluminoxane.

59. The catalyst as claimed in claim 57, wherein $R^1$–$R^4$ with the atoms joining them form one or more rings.

60. The catalyst as claimed in claim 57, wherein $R^1$, $R^2$, $R^3$ and $R^4$ are identical or different and are hydrogen, ($C_1$–$C_{10}$)alkyl, ($C_6$–$C_{14}$)aryl, ($C_1$–$C_4$)alkoxy, ($C_2$–$C_6$)alkenyl, ($C_1$–$C_6$)fluoroalkyl, a halogen or an aromatic radical having 5 or 6 ring members in the ring, at least one of which is a heteroatom and $R^5$ is ($C_1$–$C_{10}$)alkyl, or adjacent radicals $R^1$–$R^4$ form a ring with the atoms adjoining them, and $M^2$ is silicon.

* * * * *